United States Patent [19]

Crabbe et al.

[11] 3,953,470

[45] Apr. 27, 1976

[54] SUBSTITUTED PROSTAGLANDIN DERIVATIVES

[75] Inventors: Pierre Crabbe; Angel Guzman, both of Mexico City, Mexico

[73] Assignee: Syntex (U.S.A.) Inc., Palo Alto, Calif.

[22] Filed: July 11, 1974

[21] Appl. No.: 487,504

Related U.S. Application Data

[62] Division of Ser. No. 204,681, Dec. 3, 1971, Pat. No. 3,846,475.

[52] U.S. Cl. .............................................. 260/340.5
[51] Int. Cl.$^2$........................................ C07F 317/44
[58] Field of Search...................... 260/340.5, 468 D

[56] References Cited

UNITED STATES PATENTS 3,723,423   3/1973   Andersen et al............ 260/468 D X
3,821,280   6/1974   Beal et al....................... 260/468 D Primary Examiner—Richard L. Raymond
Attorney, Agent, or Firm—William B. Walker; Lawrence S. Squires; Gerard A. Blaufarb

[57] ABSTRACT

Prostaglandin analogs of the $PGF_{2\alpha}$, $PGE_2$, $PGF_{1\alpha}$ and $PGE_1$ series substituted at C-10α by a hydroxyl group, the derivatives of the $PGF_{1\alpha}$ and $PGE_1$ series further substituted at C-5,6 by a methylene or dihalomethylene group, and the 10,11-ketals thereof and methods of preparing such compounds. 9α,15α-Dihydroxy-10α,11α-isopropylidenedioxyprosta-5,13-dienoic acid, 9-keto-10α,11α-isopropylidenedioxy-15α-hydroxyprosta-5,13-dienoic acid and 5,6-methylene-9α,15α-dihydroxy-10α,11α-isopropylidenedioxyprost-13-enoic acid are representative of the class. Also included are the corresponding esters, ethers, pharmaceutically acceptable salts and amides. These compounds possess prostaglandin-like activity and thus are useful in the treatment of mammals, where prostaglandins are indicated.

14 Claims, No Drawings

SUBSTITUTED PROSTAGLANDIN DERIVATIVES

This is a division of application Ser. No. 204,681, filed Dec. 3, 1971, now U.S. Pat. No. 3,846,475, issued Nov. 5, 1974.

BACKGROUND OF THE INVENTION

1. The Invention

This invention relates to prostaglandin derivatives and intermediates for such derivatives and to methods of preparing such intermediates and derivatives. In a further aspect this invention relates to 10-substituted prostaglandin derivatives thereof and to methods of preparing such derivatives. In a still further aspect the invention relates to 10-substituted prostaglandins of the $PGE_1$, $PGE_2$, $PGF_{1\alpha}$ and $PGF_{2\alpha}$ series, the corresponding 5,6-substituted derivatives of such $PGE_1$ and $PGF_{1\alpha}$ series, and esters and ethers thereof and methods of preparing such 10-substituted prostaglandins.

In another aspect this invention relates to amide derivatives and pharmaceutically acceptable salts of such 10-substituted prostaglandins.

2. The Prior Art

Prostaglandins are a group of chemically related 20-carbon chain hydroxy fatty acids having the basic skeleton of prostanoic acid:

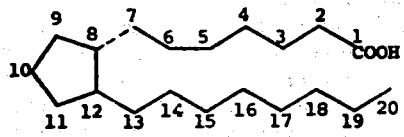

The prostaglandins having a keto group at the C-9 position are known as the PGE series, those having a hydroxyl group in place of the keto group are known as the PGF series and are further designated by an $\alpha$ or $\beta$ suffix to indicate the configuration of the hydroxyl group at said position. The natural compounds are the $\alpha$-hydroxy substituted compounds. They may contain different degrees of unsaturation in the molecule, particularly at C-5, C-13 and C-17, the unsaturation is also indicated by a suffix. For a review on prostaglandins and the definition of primary prostaglandins, see for example S. Bergstrom, Recent Progress in Hormone Research 22 pp. 153–175 (1966) and Science 157, 382 (1967) by the same author.

Prostaglandins are widely distributed in mammalian tissues and have been isolated from natural sources in very small amounts. In addition a number of the natural occurring prostaglandins have been prepared by chemical synthesis; note, for example, J. Am. Chem. Soc. 91, 5675 (1969), J. Am. Chem. Soc. 92, 2586 (1970) and J. Am. Chem. Soc. 93, 1489–1493 (1971) and reference cited therein, W. P. Schneider et al, J. Am. Chem. Soc. 90, 5895 (1968), U. Axen et al, Chem. Commun, 303 (1969), and W. P. Schneider, Chem. Commun. 304 (1969).

Because of the remarkable range of biological and pharmacological properties exhibited by this family of compounds, a great deal of interest has focused upon such compounds and accordingly we have discovered a new group of prostaglandin derivatives which exhibit general prostaglandin pharmacological and biological properties.

SUMMARY

In summary the compounds of the invention can be represented by the following generic formula:

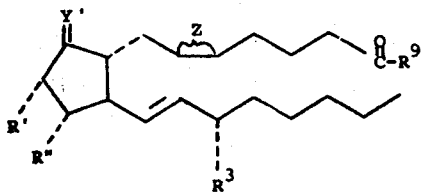

wherein Y' is keto or the group

wherein $OR^4$ is hydroxy or hydrolyzable ester or ether; $R^3$, R' and R'' are independently selected from the group of hydroxy, hydrolyzable esters, and hydrolyzable ethers, or R' and R'' together form the group

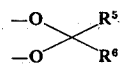

wherein $R^5$ and $R^6$ are independently hydrogen, lower alkyl, aryl, or $R^5$ and $R^6$ together with the carbon atom to which they are joined form a cycloalkyl group having 5 to 6 ring carbon atoms; $R^9$ is hydroxy, carbonylamino derivative, or the group

is a hydrolyzable ester; and Z represents a saturated linkage, a cis carbon=carbon double bond or the group

wherein X and Y are each hydrogen or fluorine or chlorine.

Also encompassed within the invention are pharmaceutically acceptable salts thereof.

The processes of the invention can be best summarized by reference to the respective flow sheets which are set forth herein below in the Further Description of the Invention.

FURTHER DESCRIPTION OF THE INVENTION AND PREFERRED EMBODIMENTS

The compounds of the invention can be represented by the following sub-generic formulas:

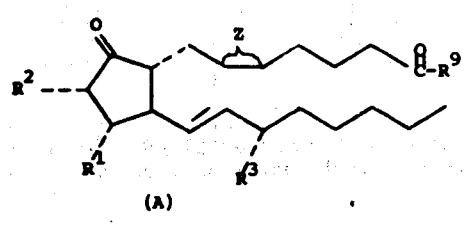

(A)

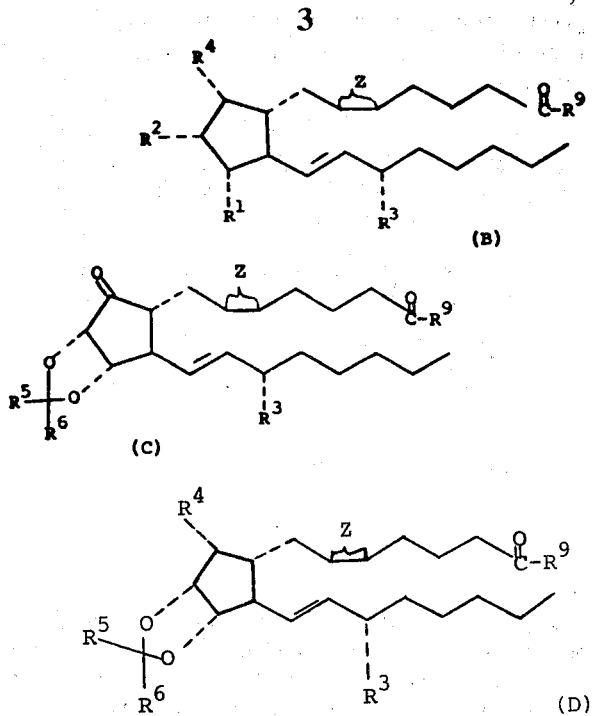

(B)

(C)

(D)

wherein each of $R^1$, $R^2$, $R^3$ and $R^4$ are independently selected from the group of hydroxy, hydrolyzable esters having from 2 through 12 carbon atoms and hydrolyzable ethers having from 1 through 12 carbon atoms; Z represents a saturated linkage, a cis carbon-carbon double bond or the group

wherein X and Y are independently selected from the group of hydrogen, fluorine and chlorine; and the wavy lines indicate that the group can be in either α or β configuration or mixtures thereof; $R^5$ and $R^6$ are each hydrogen, lower alkyl, aryl, or $R^5$ and $R^6$ together with the carbon atom to which they are joined form a cycloalkyl group having 5 or 6 ring carbon atoms; and $R^9$ is selected from the group of hydroxy and groups having the formula

wherein $R^{10}$ and $R^{11}$ are independently selected from the group of hydrogen, lower alkyl, hydroxy(lower alkyl), aryl or $R^{10}$ and $R^{11}$ together with the nitrogen atom to which they are joined form a nitrogen heterocyclic having from 5 through 7 ring atoms having 1 or 2 hetero atoms selected from the group consisting of nitrogen, oxygen and sulfur and wherein at least one of said hetero atoms is nitrogen, or the group

is a hydrolyzable ester having from 2 through 12 carbon atoms; and the dotted lines represent the α-configuration, and when one of X or Y is hydrogen the other is also hydrogen.

Also encompassed within the invention are pharmaceutically acceptable salts of the above compounds of formulas A, B, C and D.

The above compounds and salts of the invention have asymmetric centers and thus exist as optical isomers. Correspondingly the above formulas are intended to represent the respective individual (d) and (l) isomers as well as racemic mixtures of such isomers and accordingly the individual optical isomers as well as mixtures of such isomers are encompassed within the invention.

Unless expressly stated to the contrary, the following terms, as used herein above and below, have the following meanings. The term lower alkyl refers to alkyl groups having from 1 through 6 carbon atoms and includes both straight chain and branched chain alkyl groups. Typical alkyl groups thus include, for example, methyl, ethyl, pentyl, isopropyl and the like. The terms hydroxy(lower alkyl) refers to the group —ROH wherein R is lower alkyl. The term alkoxy refers to the group —OR wherein R is lower alkyl. The term halo refers to the group of fluoro, chloro, bromo and iodo. The term hydrolyzable ester refers to esters having from 2 through 12 carbon atoms derived from hydrocarbon carboxylic acids. The esters can be completely saturated or possess varying degrees of saturation and can be optionally substituted with pharmaceutically acceptable functional groups such as, for example, nitro and amino groups. Typical hydrolyzable esters include, for example, acetate, propionate, butyrate, valerate, caproate, enanthate, caprylate, perlargonate, acrylate, undecenoate, phenoxyacetate, benzoate, phenylacetate, diphenylacetate, diethylacetate, trimethylacetate, t-butylacetate, trimethylhexanoate, methylneopentylacetate, cyclohexylacetate, cyclopentylpropionate, adamantoate, glycolate, methoxyacetate, hemisuccinate, hemiadipate, hemi-β,β-dimethylglutarate, acetoxyacetate, 2-chloro-4-nitrobenzoate, aminoacetate, diethylaminoacetate, piperidinoacetate, β-chloropropionate, trichloroacetate, β-chlorobutyrate, and the like. The term hydrolyzable ether refers to ether groups having from 1 through 12 carbon atoms and can be optionally substituted with pharmaceutically acceptable functional groups such as, for example, nitro and amino groups. The ethers can be saturated or possess varying degree of unsaturation. Typical hydrolyzable ethers include, for example, methoxy, ethoxy, propoxy, 2-propoxy, cyclopropoxy, butoxy, 2-butoxy, t-butoxy, cyclobutoxy, pentoxy, 3-pentoxy, cyclopentoxy, hexoxy, cyclohexoxy, methoxymethoxy, 2-methoxyethoxy, 2-ethoxyethoxy, 2-aminoethoxy, 2-chloroethoxy, 3-fluorobutoxy, 2-acetoxyethoxy, 3-nitropropoxy, 3-aminocyclobutoxy, 4-hexylcyclohexoxy, 2-phenoxyethoxy, phenoxy, tolyloxy, chlorophenoxy, m,m'-dimethylphenoxy, p-nitrophenoxy, β-chloropropoxy, p-aminophenoxy, tetrahydrofuran-2'-yloxy, tetrahydropyran-2'-yloxy, and the like.

The term aryl refers to a group having a total of up to 16 carbon atoms and containing one aromatic ring having up to 10 carbon atoms optionally substituted with one or more pharmaceutically acceptable functional groups selected from the group of hydroxy, lower alkyl hydrolyzable ester, lower alkyl or halo. Typical aryl groups include, for example, phenyl, o-tolyl, p-isopropylphenyl, p-, o-, m-trimethylphenyl, p-hydroxyphenyl, p-acetoxyphenyl, p-nitrophenyl, p-fluorophenyl, p-chlorophenyl and the corresponding ortho and meta isomers, and the like.

The term N-heterocycle or nitrogen heterocycle refers to both saturated and unsaturated heterocyclics having from 5 through 7 ring atoms, one of which is nitrogen and which can optionally also contain a second heterocycle ring atom selected from the group of nitrogen, sulfur and oxygen. Also encompassed within the term are substituted N-heterocyclics having one or two substituents independently selected from the group of lower alkyl, hydroxylower alkyl, and halo. Typical N-heterocycles thus include, for example, those groups having the formulas:

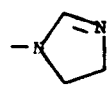 ; 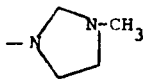

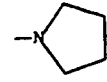 ; 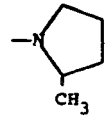

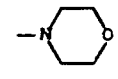 ; 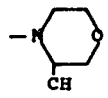

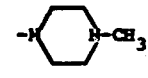 ; 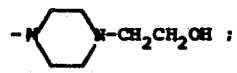

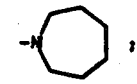 ; 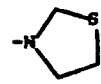

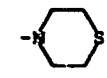 ; 

and the like.

The term "pharmaceutically acceptable" refers to groups which do not significantly adversely affect the pharmaceutical properties of the parent compounds. The term pharmaceutically acceptable salts refer to base addition salts of the carboxy acid function of the parent prostaglandin and which do not significantly adversely affect the pharmaceutical properties of the parent compound. Typical pharmaceutical base addition salts include, for example, metal salts such as sodium potassium, calcium, magnesium aluminum and the like, as well as organic amine salts such as triethylamine, 2-dimethylamino ethanol, 2-diethylamino ethanol, lysine, arginine, caffeine, procaine, N-ethylpiperidine, hydramine and the like.

Typical illustrations of the compounds and salts of the invention can be had by reference to the appropriate Examples set forth herein below. The preferred $R^1$, $R^2$, $R^3$ and $R^4$ groups are those wherein $R^1$, $R^2$, $R^3$ and $R^4$ are independently selected from the group of hydroxy and hydrolyzable lower alkyl esters having from 2 through 7 carbon atoms and especially hydroxy and acetoxy. $R^5$ and $R^6$ are preferably each methyl. The preferred $R^9$ groups are hydroxy, amino, diethylamino, and β-hydroxyethylamino and especially hydroxy. The preferred

groups are lower alkyl esters.

The particularly preferred compounds of formula A, of the invention, are:
9-keto-10α,11α,15α-trihydroxyprosta-5,13-dienoic acid;
9-keto-10α,11α,15α-trihydroxyprost-13-enoic acid;
6,7-methylene-9-keto-10α,11α,15α-trihydroxyprost-13-enoic acid; and
5,6-difluoromethylene-9-keto-10α,11α,15α-trihydroxyprost-13-enoic acid.

The particularly preferred compounds of formula B, of the invention, are:
9α,10α,11α,15α-tetrahydroxyprosta-5,13-dienoic acid;
9α,10α,11α,15α-tetrahydroxyprost-13-enoic acid;
5,6-methylene-9α,10α,11α,15α-tetrahydroxyprost-13-enoic acid; and
5,6-difluoromethylene-9α,10α,11α,15α-tetrahydroxyprost-13-enoic acid.

The particularly preferred compounds of formula C, of the invention, are:
9-keto-10α,11α-isopropylidenedioxy-15α-hydroxyprosta-5,13-dienoic acid; and
9-keto-10α,11α-isopropylidenedioxy-15α-hydroxyprost-13-enoic acid.

The particularly preferred compounds of formula D, of the invention, are:
9α,15α-dihydroxy-10α,11α-isopropylidenedioxyprosta-5,13-dienoic acid;
9α,15α-dihydroxy-10α,11α-isopropylidenedioxyprost-13-enoic acid;
5,6-methylene-9α,15α-dihydroxy-10α,11α-isopropylidenedioxyprost-13-enoic acid; and
5,6-difluoromethylene-9α,15α-dihydroxy-10α,11α-isopropylidenedioxyprost-13-enoic acid.

The preferred pharmaceutically acceptable salts are the sodium salts and correspondingly the particularly preferred salts are the corresponding sodium salts of the particularly preferred compounds of formulas A, B, C and D.

The compounds of the invention, except for the 5,6-methylene or halomethylene substituted compounds can be prepared by the following schematically illustrated process:

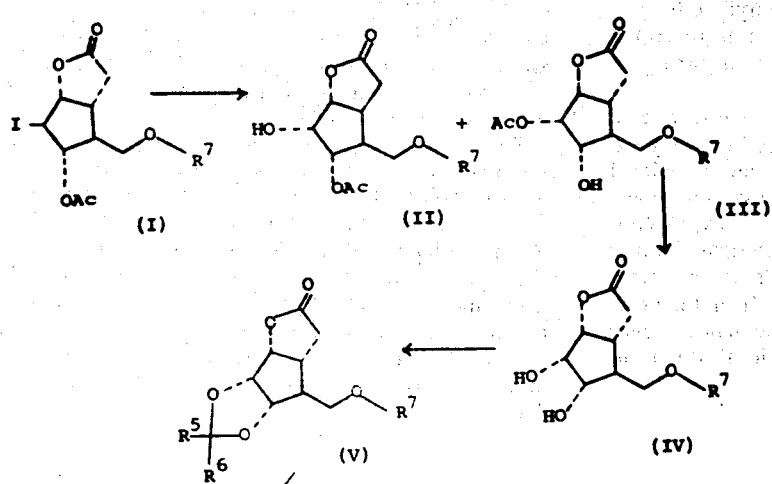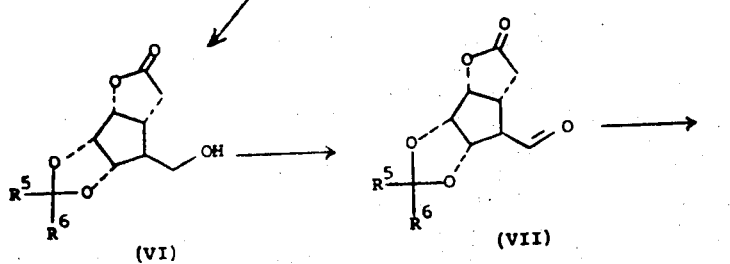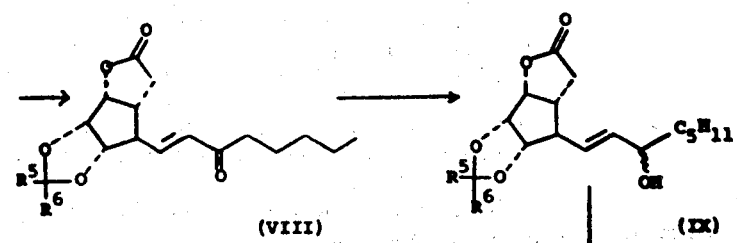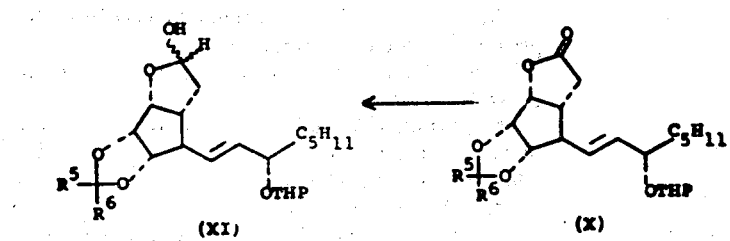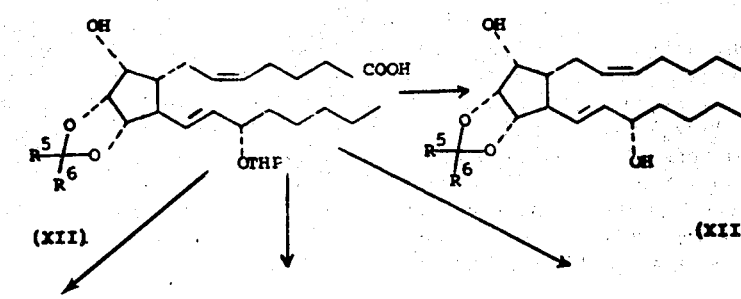

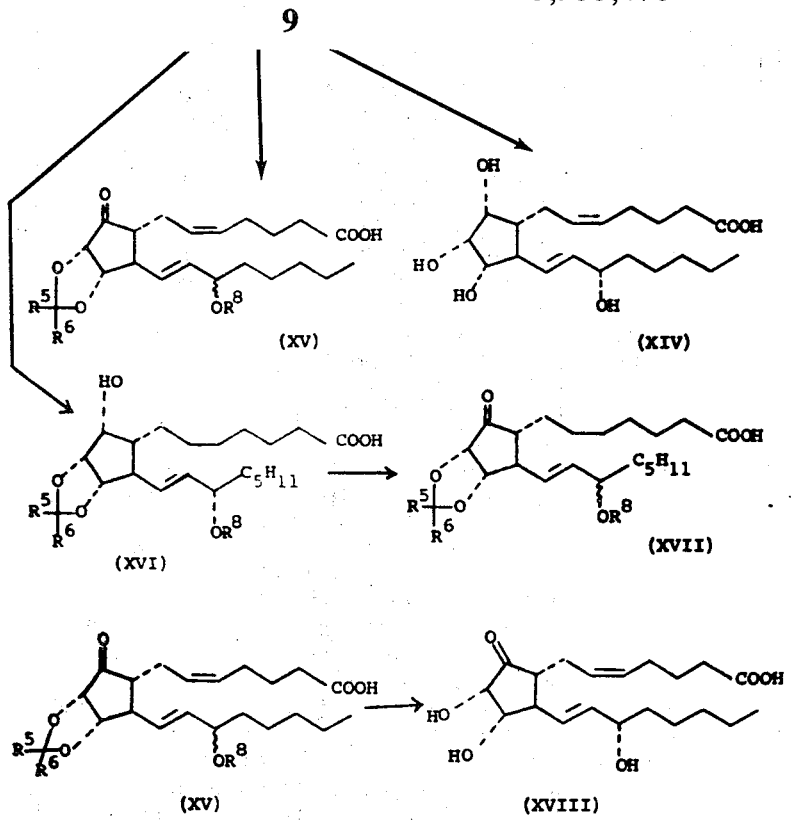

wherein Ac is acetyl; THP is tetrahydropyranyl; $R^7$ represents methyl or benzyl; $R^8$ represents hydrogen or tetrahydropyranyl; $R^5$ and $R^6$ are as defined herein above; and the wavy line ( ) indicates the $\alpha$ or $\beta$ configuration, or mixtures thereof and the dotted line (---) indicates the $\alpha$-configuration.

In practicing the process outlined above, the starting iodo lactones of formula I, namely (2'$\alpha$-hydroxy-4'$\alpha$-acetoxy-3'$\beta$-iodo-5'$\beta$-benzyloxymethylcyclopent-1'$\alpha$-yl)-acetic acid 1,2'-lactone (I, $R^7$ = benzyl) or (2'$\alpha$-hydroxy-4'$\alpha$-acetoxy-3'$\beta$-iodo-5'-methoxymethylcyclopent-1'$\alpha$-yl)-acetic acid 1,2'-lactone (I, $R^7$ is methyl) can be treated with silver acetate in aqueous acetic acid to yield a mixture of the hydroxy acetates (II) and (III).

This reaction is preferably conducted at reflux temperature for a period of time of the order of 1 to several hours, preferably for about two hours. Typically about from 1 to 4 molar equivalents of silver acetate is used per molar equivalent of starting material I, and preferably about 2.5 molar equivalents.

The product (II and III) can be separated from the reaction mixture by conventional techniques, for example, by separating the silver iodide formed by filtration, washing the precipitate with an organic solvent, and evaporation of the filtrates under reduced pressure.

The compounds of formulas II and III can be saponified under alkaline conditions, using an alkali metal hydroxide or carbonate in a lower aliphatic alcohol, to produce the corresponding dihydroxy compound of formula IV. Best results are typically obtained using anhydrous potassium carbonate and conducting the reaction at about from 5° to 20° C, for about from 2 to 4 hours.

The dihydroxy lactone IV can be condensed with a suitable ketone in the presence of an acid catalyst to afford the corresponding ketal of formula V. In this reaction the ketone used can serve as both reagent and solvent, or alternatively the reaction can be carried out in the presence of an inert cosolvent. Suitable ketones which can be used include, for example, acetone, methylethyl ketone, diethylketone, acetophenone, cyclohexanone and the like. Suitable catalysts which can be used include strong organic and inorganic acids such as, for example, p-toluenesulfonic acid, hydrochloric acid, sulfuric acid, perchloric acid and the like. The reaction is preferably conducted in the presence of an inert organic solvent. Suitable inert organic solvents which can be used include, for example, tetrahydrofuran, dioxane, 2,2-dimethoxypropane and the like. Typically the reaction is conducted at about from 15° to 25° C room temperature, for about from 1 to 5 hours. Particularly good results are obtained by conducting the treatment at about 20° C or 2½ hours using a mixture of the ketone reagent, e.g. acetone with 2,2-dimethoxypropane in the presence of p-toluenesulfonic acid.

The ketal (V) can be conveniently isolated by adding a few drops of pyridine to the reaction mixture, followed by evaporation to dryness and crystallization of the residue from suitable solvents, e.g., acetone, ethylacetate, and the like.

The 5'-hydroxymethyl compounds of formula VI can be prepared by cleavage of 5'-benzyloxymethyl or 5'-methoxymethyl group from the corresponding ketals of formula V.

In the case of the compounds of (V) wherein $R^7$ is benzyl, cleavage can be conveniently effected by hydrogenolysis in the presence of a metal catalyst of group VIII of the Periodic Table, such as palladium, platinum or nickel, and preferably in the presence of a catalytic amount of perchloric acid, to produce the hydroxymethyl compound of formula VI. The preferred metal catalyst is palladium charcoal. Typically the hydrogenolysis is conducted in a suitable inert organic solvent such as acetone, ethyl acetate, methanol, and the like, at temperatures of about from 15° to 25° C under atmospheric pressure or higher, until the absorption of hydrogen ceases.

The compounds of formula V wherein $R^7$ is lower alkyl, e.g., methyl, can be converted into the hydroxymethyl compound of formula VI by cleavage with boron tribromide in methylene chloride. Typically cleavage is conducted at temperatures in the range of about from between approximately −78° to 0° C, for about from one-half to 3 hours and preferably about 1 hour. The product VI can be conveniently isolated from the reaction mixture by destruction of the excess boron tribromide with sodium bicarbonate followed by neutralization with base extraction with a suitable organic solvent immiscible with water, e.g., methylene chloride or ethyl acetate; the product can be further purified by chromatography.

The hydroxymethyl compound of formula (VI) can be oxidized to the corresponding formyl derivative of formula VII by treatment with a suitable oxidant. Since the compounds are sensitive to acid, acid conditions are preferably avoided. Suitable oxidants are, for example, chromium trioxide-pyridine complex, chromium trioxide-dipyridine complex (Collins' reagent) or dicyclohexylcarbodiimide or diisopropylcarbodiimide in dimethylsulfoxide (Moffatt's reagent). In the preferred embodiments, this oxidation is effected using chromium trioxide-dipyridine complex prepared as described by J. C. Collins et al in Tetrahedron Letters, 3363 (1968). Isolation of the aldehyde product (VII) can be accomplished by conventional procedures, however, preferably acid conditions should be avoided as otherwise some hydrolysis of the ketal ring can take place.

The crude aldehyde (VII) can be transformed stereospecifically into the trans enone lactone of formula VIII via a modified Wittig reaction. Procedures for the Wittig reaction are well known in the art, see for example, S. Trippet et al, Adv. in Organic Chemistry, Vol. 1, pp. 83–102, S. Trippet, Quarterly Reviews, Vol. 17, pp. 400–440. The reagent used is the sodium anion of dimethyl-2-oxoheptylphosphonate in dimethoxyethane, which is prepared in accordance with the method described by E. Corey et al, J. Am. Chem. Soc., 88, 5654 (1966). Typically the reaction is conducted under an inert atmosphere, e.g. under nitrogen or argon atmosphere, at temperatures between 0° C and 40° C, preferably at room temperature or below, using at least one molar equivalent of the reagent per mole of aldehyde (VII), and preferably 1.2 to 2 moles. This reaction is carried out for a period of about from 1 to 4 hours, depending on the temperature and concentration of the reaction mixture. In the preferred conditions, the reaction is conducted at room temperature for about from 1 to 2 hours, longer reaction times give rise to more elimination products. The enone VIII can be recovered from the reaction mixture by neutralization of the excess base with acetic acid to pH~7, followed by evaporation of the solvent under hight vacuum, at low temperature, or by adding water and extracting the product with suitable solvent immiscible with water, e.g., methylene chloride, diethyl ether and the like, followed by evaporation of the solvent. The crude product can be further purified by conventional techniques, such as recrystallization or chromatography on silica gel or thin-layer chromatography.

The enone of formula VIII can be selectively reduced with a solution of zinc borohydride in an ether solvent such as dimethoxyethane, to yield a mixture of the 15α-hydroxy lactone and its 15β epimer (R and S isomers) compounds of formula IX. The reaction is conducted at temperatures in the range of about from 5° to 20° C for about from 15 minutes to 3 hours, preferably using an excess of zinc borohydride. The zinc borohydride reagent solution can be prepared from freshly fused zinc chloride and sodium borohydride in dimethoxyethane.

The epimeric 15α- and 15β-hydroxy compounds can be separated, if desired, by conventional chromatography on silica gel or by thin layer chromatography. In addition, the 15β-epimer can be reverted to the starting enone VIII by reaction with manganese dioxide in methylene chloride or chloroform or with 2,3-dichloro-5,6-dicyano-1,4-benzoquinone in dioxane, according to known methods for the preparation of α,β-unsaturated ketones from allylic alcohols.

Alternatively the reduction step can be carried out via treatment with a borohydride ion (conveniently prepared by reaction of a trialkylborone derivative from either racemic or (+)-limonene, t-hexylborane and t-butyl lithium) in the presence of hexamethylphosphoramide at about from −130° to 100° C and preferably 120° C. In this the predominate product is the 15α-alcohol (IX) and only small amounts of the 15β-epimer (IX) is obtained.

The 15α-hydroxy compound of formula IX can be etherified with dihydropyran in methylene chloride, in the presence of catalytic amounts of an acid catalyst (e.g., p-toluenesulfonic acid), under anhydrous conditions, to produce the tetrahydropyranyloxy derivative of formula X. Typically the reaction is conducted at about room temperature for about 15 minutes, using about 3 molar equivalents of dihydropyran in an inert organic solvent, e.g., using methylene chloride. A larger excess of dihydropyran, or longer reaction periods produce polymerization of this reagent.

The product can be isolated by adding a few drops of pyridine to the product reaction mixture, followed by conventional extraction and evaporation of the organic extract.

The isomeric lactone of formula XI can be prepared by reduction of the 15α-tetrahydropyranyloxy-lactone (X) with about from 1.1 to 3 molar equivalents of diisobutylaluminum hydride in a suitable inert organic solvent. Typically the reduction is conducted at about from −30° to −70° C, preferably at about −60° C, for a period of about from 10 to 30 minutes, preferably using about 2 molar equivalents of the diisobutylaluminum hydride. Suitable inert organic solvents for this reaction include, for example, the aromatic hydrocarbons such as toluene or xylene.

The product can be isolated from the reaction mixture by conventional separation procedures and can be used for the next step with or without separation of the isomers.

The 15-tetrahydropyranylether-10,11-ketal of 10α-hydroxy-PGF$_{2\alpha}$ (XII) can be prepared by condensation of the crude lactol XI with the Wittig reagent derived from 5-triphenylphosphoniopentanoic acid and sodium methylsulfinylcarbanion in dimethylsulfoxide solution.

Typically this reaction is conducted under anhydrous conditions for about 2 to 24 hours at temperatures in the range of about from 15° to 50° C. This reaction is preferably carried out under an inert atmosphere, e.g., under argon or nitrogen atmosphere. Typically the triphenylphosphoniopentanoic acid is used in an amount varying from about 2 to about 5 moles per mole of starting lactol (XI) and the amount of sodium methylsulfinyl carbanion vary between about 2 to about 10 moles. In the preferred embodiments 2.5 molar equivalents of the acid reagent and 5 molar equivalents of the carbanion reagent are used per mole of lactol (XI). The product is obtained as the sodium salt soluble in water, which can be converted to the free acid by acidification with oxalic acid or another weak acid to pH 2, followed by conventional extraction and evaporation. Preferably the prostaglandin derivative (XII) is further purified by thin-layer chromatography. The 5-triphenylphosphoniopentanoic acid can be prepared according to the procedure described by R. Greenwald et al, in J. Org. Chem. 28, 1128 (1963), from 5-bromopentanoic acid and triphenylphosphine in acetonitrile. The sodium methylsulfinyl carbanion can be obtained from sodium hydride and dimethylsulfoxide, stirring the mixture at about 75° C until the evolution of gas ceases. Generally, it is preferred to prepare these reagents just prior to the reaction with the lactol of formula XI.

The compound of formula XIII (10,11-ketal of 10α-hydroxy-$PGF_{2\alpha}$) can be prepared by selectively hydrolyzing the tetrahydropyranyloxy function from the corresponding compound of formula XII, under mild acidic conditions — for example, by treatment with a weak acid (e.g., acetic acid, oxalic acid, tartaric acid and the like) in the presence of water. Preferably the starting material of formula XII is first dissolved in an inert water miscible organic solvent (e.g., tetrahydrofuran, dioxane and the like) prior to treatment with the weak acid. The hydrolysis is preferably conducted using aqueous acetic acid, at a temperature in the range of about from 0° to 50° C for about 4 to 10 hours. The preferred concentration of aqueous acetic acid is 65% wt., however, other concentrations can, of course, also be used.

Longer reaction times and/or higher temperature produce simultaneous hydrolysis of the ketal moiety, thus producing 10α-hydroxy $PGE_{2\alpha}$, compound of formula XIV.

The 15-tetrahydropyranylether 10,11-ketal of 10α-hydroxy-$PGE_2$ (XV, $R^8$ = tetrahydropyranyl) can be prepared by oxidation of the corresponding compound of formula XII with Jones reagent, Moffatt's reagent or with aqueous chromic acid in diethyl ether (H. C. Brown et al, J. Org. Chem., 36, 387 (1971)). This product can in turn be hydrolyzed under mild acidic conditions, as described herein above, to afford the corresponding 10,11-ketal of 10α-hydroxy-$PGE_2$ (XV, $R^8$ = H), or by using longer hydrolysis durations or higher temperatures of the 10α-hydroxy-$PGE_2$ compound of formula XVIII.

The $PGF_{1\alpha}$ and $PGF_1$ series of compounds of formulas XVI and XVII, wherein $R^8$ is tetrahydropyranyl, can be respectively prepared by selective hydrogenation of C-5(6) double bond of the corresponding 15-tetrahydropyranylether 10,11-ketals of 10α-hydroxy-$PGF_{2\alpha}$ and $PGE_2$ compounds of formulas XII and XV. Typically the hydrogenation is conducted in an inert organic solvent (e.g., lower aliphatic alcohols) at temperatures in the range of about from −60° to −10° C, preferably about −20° to −15° C, under atmospheric pressure in the presence of a palladium impregnated charcoal catalyst using one mole of hydrogen per mole of prostaglandin starting material. Preferably the reaction is monitored, for example, by thin-layer chromatography, and the reaction interrupted as soon as analysis indicates the presence of a minute quantity of completely saturated prostaglandin. The corresponding 10,11-ketals of 10α-hydroxy-$PGF_{1\alpha}$ and $PGE_1$ (XVI and XVII, $R^8$ is H) and the corresponding completely hydrolyzed compounds can be prepared via mild acid hydrolysis of the corresponding 15-tetrahydropyranylethers, as described herein above.

Alternatively, compound XVII can be prepared by oxidation of the 15-tetrahydropyranylether 10,11-ketal of 10α-hydroxy $PGF_{1\alpha}$ (XVI, $R^8$ = tetrahydropyranyl), according to the procedure described herein above for the 5,6-unsaturated compound followed by hydrolyzation of the tetrahydropyranyloxy moiety under mild acidic conditions.

The 5,6-methylene and halomethylene derivatives of the invention can be prepared by the following schematically illustrated process.

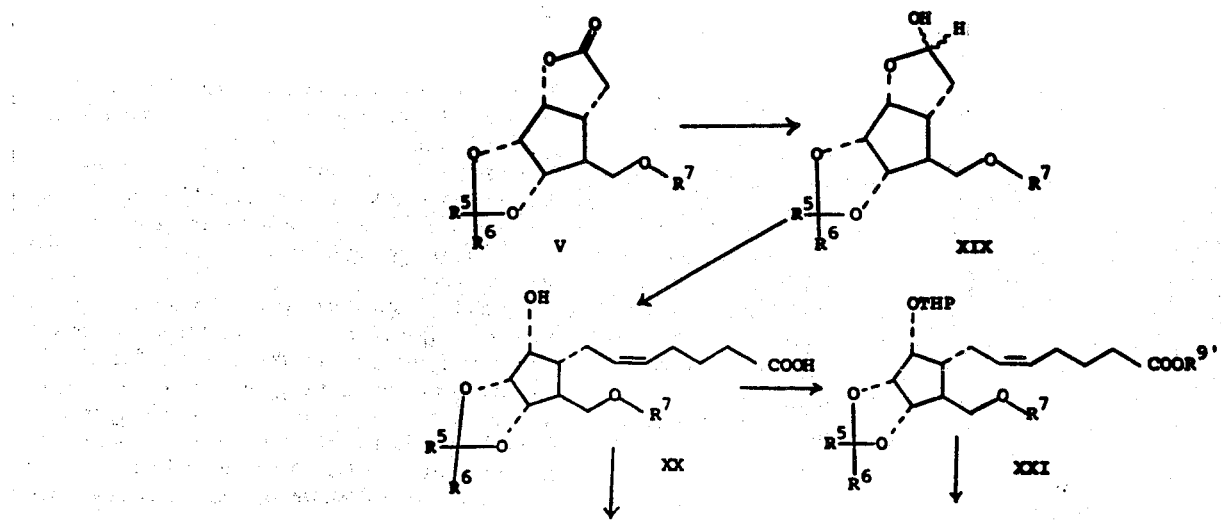

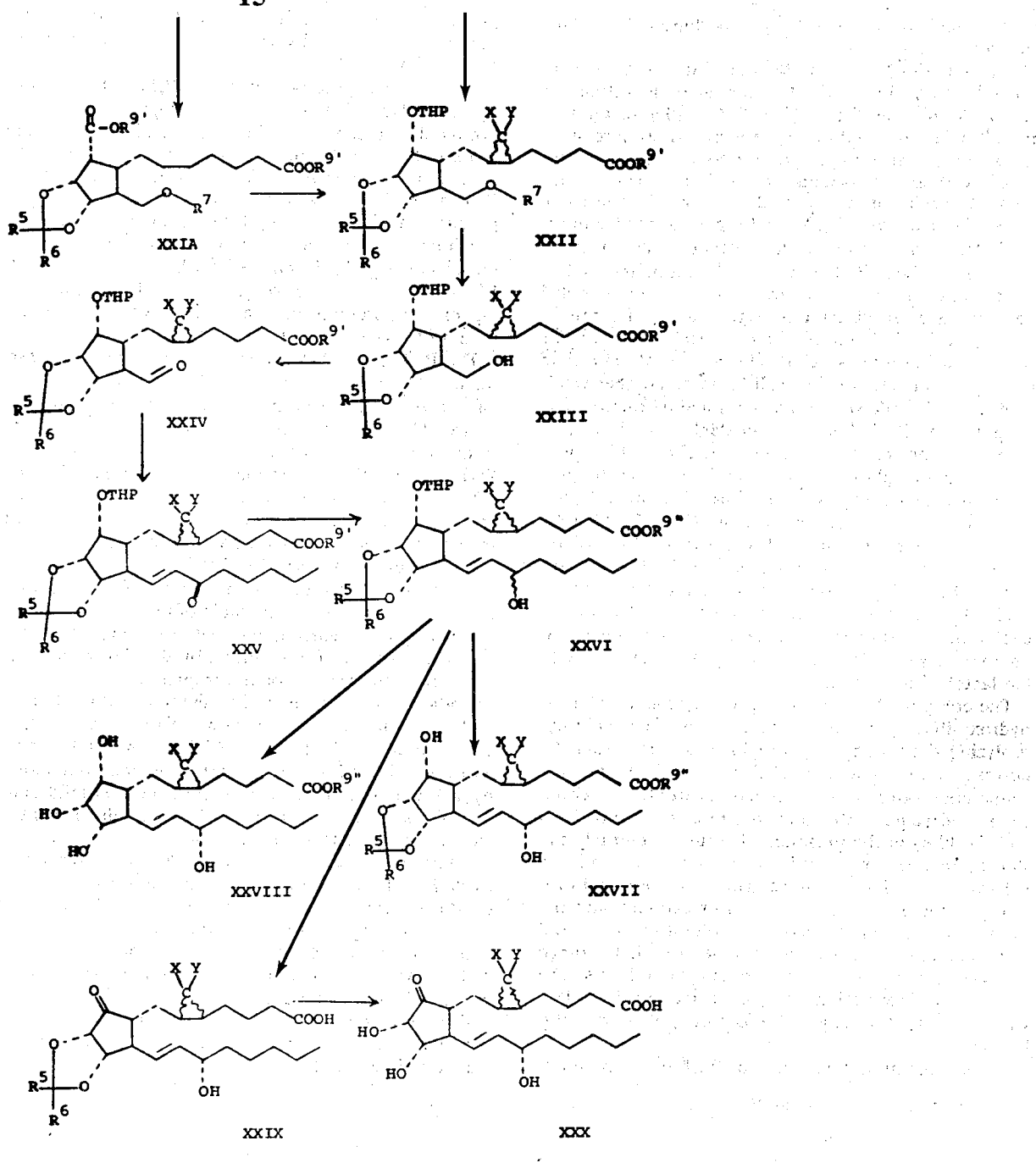

wherein $R^5$, $R^6$, $R^7$, X and Y have the above-identified meaning; $R^{9'}$ represents methyl or ethyl and $R^9$ represents hydrogen, methyl or ethyl.

The wavy lines ($\wr$) denote and include both the $\alpha$ and $\beta$ configurations or mixtures thereof.

The first step in the above process can be effected by treating a 3′,4′-ketal of (2′α, 3′α,4′α-trihydroxy-5′β-benzyloxymethylcyclopent-1′α-yl)-acetic acid 1,2′-lactone or a 3′, 4′-ketal of (2′α,3′α,4′α-trihydroxy-5′β-methoxymethylcyclopent-1′α-yl)-acetic acid, 1,2′-lactone (formula V) with about 1.1 to 3 molar equivalents of diisobutylaluminum hydride per mole of compound of formula V in a suitable organic solvent at a temperature between −30° to −70° C, for about from 15 to 30 minutes, to yield the lactol of formula XIX. Suitable organic solvents for this reaction include, for example, the aromatic hydrocarbons such as toluene, xylene and the like. The starting materials of formula V can be prepared as described herein above.

The substituted cyclopentane heptenoic acid derivative of formula XX can be prepared by condensation of the crude lactol XIX with a Wittig reagent derived from 5-triphenylphosphoniopentanoic acid in dimethylsulfoxide solution.

Typically the condensation is conducted under anhydrous conditions for about from 2 to 24 hours at temperatures in the range of about from 15° to 50° C. The reaction is preferably performed under an inert atmosphere, such as for example, nitrogen, argon and the like. The product of this treatment is a water soluble sodium salt from which the free acid can be obtained by acidification with a weak acid, e.g., oxalic acid or acetic acid to pH 2, followed by conventional extraction and evaporation. The heptenoic acid derivative can be further purified, if desired, by thin-layer chromatography.

The compounds of formula XXI can be prepared in two steps. In the first step the carboxyl group of the cyclopentane heptenoic acid compounds of formula XX is esterified by any suitable procedure. For example, esterification can be conveniently effected according to conventional procedures via treatment with a diazoalkane (e.g., diazomethane or diazoethane) in a suitable inert organic solvent, such as for example ethyl ether or methylene chloride. In the second step the free hydroxy function of the esterified product is etherified by any suitable etherification process. This can be conveniently effected via treatment with tetrahydropyran in the presence of an acid catalyst, according to the procedure described herein above.

The compounds of formula XXIA can be conveniently prepared by treating the esterified carboxy compounds of formula XX according to any suitable procedure for esterifying hydroxy groups. This can, for example, be conveniently effected via conventional procedures via treatment with an acid anhydride (e.g., acetic anhydride) in the presence of an inert organic solvent such as, for example, pyridine.

The compounds of formula XXII wherein X and Y are each hydrogen can be prepared by treating the corresponding compound of formula XXI, according to the Simmons-Smith reaction, with methylene iodide in the presence of a zinc-copper couple. Typically this treatment is conducted at about the reflux temperature of the system and preferably is conducted under an inert atmosphere. The reaction mixture is preferably monitored (for example by thin-layer chromatography) and the reaction continued until essentially complete. Also the zinc-copper couple is preferably prepared in situ, for example by the addition of zinc dust and cuprous chloride to a suitable inert organic solvent. The reactants are then preferably added directly to the zinc-copper couple mixture.

The fused dihalocyclopropyl compound of formula XXII (X and Y are independently fluorine or chlorine) can be prepared by treating the corresponding compound of formula XXI or XXIA with the desired dihalocarbene. This treatment can be conveniently effected by generating the desired dihalocarbene from the corresponding alkali metal salts of trihaloacetic acid; e.g., sodium trichloroacetate (X = Cl, Y = Cl), sodium chlorodifluoroacetate (X = F, Y = F), sodium dichlorofluoroacetate (X = F, Y = Cl).

The reaction is conducted under anhydrous conditions, at a temperature above which the particular salt employed decomposes, using an inert nonaqueous solvent of sufficient polarity to dissolve the haloacid salt. Suitable solvents include dimethoxyethane, diethylene glycol dimethyl ether, triethylene glycol dimethyl ether and the like. Generally, the reaction is performed at temperatures in the range of about from 80°C to 180°C, depending upon the trihaloacetate employed, for about 30 minutes to 2 hours.

Likewise, other reagents known to generate dihalocarbenes such as, for example, trimethyl (trifluoromethyl) tin, phenyl (trichloromethyl) mercury, phenyl (bromodichloromethyl) mercury, phenyl (trifluoromethyl) mercury and the like, in the presence of sodium iodide, can also be used. In this instance the reaction is typically conducted at temperatures of about from 75 to 110°C, for about 2 to 18 hours, in an aromatic hydrocarbon solvent.

Thus for example by refluxing compound of formula XXI with phenyl (trifluoromethyl) mercury and sodium iodide, using benzene as solvent, for about 18 hours, the difluoromethylene derivative is obtained (XXII, X = F, Y = F).

In each instance the halomethylene derivative is typically a mixture of $\alpha$ and $\beta$ isomers which, if desired, can then be purified by chromatography to separate the individual isomers. These isomers are typically obtained in approximately equal amounts.

Typically the resulting product will be esterified at the 9-position. If desired. 9-position free hydroxy group can be obtained by mild base hydrolysis — for example by treatment with a dilute aqueous sodium carbonate solution. The corresponding 9-position tetrahydropyranyl ethers of formula XXII can then be prepared by treatment of the parent free hydroxy compound according to the etherification procedures previously desired herein.

Compounds of formula XXII (mixture of $\alpha$ and $\beta$-methylene or halomethylene compounds, or the separated isomers) can then be converted into the corresponding hydroxymethyl compounds of formula XXIII. The compounds of formula XXII ($R^7$ = benzyloxy) can be conveniently cleaved by hydrogenolysis in the presence of a hydrogenation catalyst, to produce the hydroxymethyl compound of formula XXIII. This hydrogenolysis is conducted in a suitable inert organic solvent such as acetone, ethyl acetate, methanol, and the like, at room temperature under atmospheric pressure or higher, until the absorption of hydrogen ceases.

When $R^7$ is methoxy, compound XXII can be conveniently converted into the hydroxymethyl compound of formula XXIII by cleavage with boron tribromide in methylene chloride, at a temperature in the range of about from −78° to 0° C, for a period of time of about one hour. The product is isolated from the reaction mixture by destruction of the excess boron tribromide with ethereal sodium bicarbonate, followed by neutralization with base and extraction with an adequate organic solvent immiscible with water, e.g., methylene chloride or ethyl acetate; the product can be further purified by chromatography.

The hydroxymethyl compound (XXIII) can be oxidized to the corresponding formyl derivative, of formula XXIV. Since the compounds are sensitive to acid, acid conditions are preferably avoided. Suitable oxidants include, for example, chromium trioxide-pyridine complex, chromium trioxide-di-pyridine complex (Collins' reagent) or dicyclohexylcarbodiimide or diisopropylcarbodiimide in dimethylsulfoxide (Moffatt's reagent). In the preferred embodiments, this oxidation is effected using chromium trioxide-dipyridine complex, prepared as described by J.C. Collins et at, in Tetrahedron Letters, 3363 (1968). Isolation of the aldehyde compound can be accomplished by conventional procedures, however, acid conditions should be avoided, otherwise some hydrolysis of the ketal ring can take place.

The crude aldehyde XXIV can be transformed stereospecifically into the trans enone lactone of formula XXV. This transformation involves a modified Wittig reaction. The reagent used is the sodium anion of dimethyl-2-oxoheptylphosphonate in dimethoxyethane, which is conveniently prepared in accordance with the method described by E. Corey et al, J. Am. Chem. Soc., 88, 5654 (1966). The reaction is typically conducted under an inert atmosphere, i.e., under nitrogen or argon atmosphere, at temperatures between 0° C and 40° C, preferably at room temperature or below, using at least one molar equivalent of the reagent per mole of aldehyde, and preferably 1.2 to 2 moles. This reaction is carried out for a period of about 1 to 4 hours, depending upon the temperature and concentration of the reaction mixture. In the preferred conditions, the reaction is conducted at room temperature for two hours or less as longer reaction times give rise to more elimination products. The enone is typically recovered from the reaction mixture by careful neutralization of the excess base with acetic acid to pH 7, followed by evaporation of the solvent under high vacuum, at low temperature, or by adding water and extracting the product with an adequate solvent immiscible with water, e.g., methylene chloride, diethyl ether and the like, followed by evaporation of the solvent. If desired, the crude product can be further purified by conventional techniques, such as recrystallization or chromatography on silica gel or thin-layer chromatography.

The enone of formula XXV can be reduced with a solution of zinc borohydride in an ether solvent such as dimethoxyethane, to yield a mixture the $15\alpha$-hydroxy and $15\beta$-hydroxy derivatives (R and S isomers, ratio ca 1:1) compounds of formula XXVI, ($R^{9\prime\prime}$ = methyl or ethyl). Typically the reaction is conducted at room temperature or below for about 15 minutes to about two hours, depending upon the temperature used. The zinc borohydride reagent solution is preferably prepared from freshly fused zinc chloride and sodium borohydride in dimethoxyethane. An excess of this reagent is used for the reduction of the enone.

If desired, the epimeric $15\alpha$- and $15\beta$-hydroxy compounds can be separated by conventional chromatography on silica gel, by thin-layer chromatography or fractional crystallization. The $15\beta$-epimer can be reverted to the starting enone XXV by reaction with manganese dioxide in methylene chloride or chloroform or with 2,3-dichloro-5,6-dicyano-1,4-benzoquinone in dioxane, well known methods for the obtention of $\alpha,\beta$-unsaturated ketones from allylic alcohols.

Alternatively this reduction can be carried out with a borohydride ion obtained by reaction of a trialkylborane derived from either racemic or (+)-limonene, t-hexylborane and t-butyl lithium, conducting the reaction in the presence of hexamethylphosphoramide at approximately −120° C. In this case the $15\alpha$-alcohol predominates, yielding only small amounts of the $15\beta$-epimer.

The compounds of formula XXVII can be prepared by selectively hydrolyzing under mild acidic conditions (e.g., using a weak acid such as acetic acid, oxalic acid, tartaric acid and the like in the presence of water), the tetrahydropyranyloxy moiety in compounds of formula XXVI ($R^{9\prime\prime}$ = methyl, ethyl). The starting compound is preferably dissolved in an organic solvent miscible with water, e.g., tetrahydrofuran, dioxane and the like, before addition of the dilute acid to produce the corresponding 10,11-ketal of 5,6-methylene $9\alpha,10\alpha11\alpha1$-$5\alpha$-tetrahydroxy-prost-13-enoic acid alkyl ester, compounds of formula XXVII ($R^{9\prime\prime}$ = methyl, ethyl). This hydrolysis is preferably conducted using aqueous acetic acid, temperatures of about from 0° to 50° C for about 4 to 10 hours, depending upon the temperature used. The preferred concentration of aqueous acetic acid is 65% wt., however, other concentrations are also practical.

Longer reaction times and/or higher temperatures produce simultaneous hydrolysis of the ketal moiety, thus producing compounds of formula XXVIII ($R^{9\prime\prime}$ = methyl, ethyl).

The alkyl ester groups in compounds of formulas XXVI, XXVII and XXVIII can be removed by hydrolysis under alkaline conditions (e.g., using a dilute solution of an alkali-metal hydroxide or alkali-metal carbonate in a lower aliphatic alcohol, at room temperature or below, for about 2 to about 6 hours, followed by acidification with acetic or oxalic acid) to give the free acids (XXVI, XXVII and XXVIII, $R^{9\prime\prime}$ = H). Best results are typically obtained using potassium carbonate in methanol solution for about 4 hours at room temperature.

The 15-position esters of 5,6-methylene and halomethylene derivatives of the $PGE_1$ series can be prepared by esterifying the corresponding compounds of formula XXVI by conventional procedures. This can, for example, be conveniently effected by treatment with acetic anhydride in pyridine or acetyl chloride. If desired, the 9-position ether group (e.g., tetrahydropyran) can then be removed by treatment with acetic acid as previously described.

The 9-ketone 5,6-methylene or halomethylene compounds, of the invention, can be prepared by oxidation of the corresponding $9\alpha$-hydroxy compounds of the invention. The oxidation can be effected according to conventional procedures, for example, by treatment with Jones reagent, or Collins reagent, or Moffatt's reagent or by treatment with chromic acid in diethyl ether.

The free carboxy acid compounds can be prepared by conventional hydrolysis, under mild basic conditions, of the corresponding alkyl esters. This can, for example, by treatment with potassium carbonate in methanol, at about room temperature for about 6 hours. In this case, ester functions at both the C-15 and/or the C-1 position are hydrolyzed. Thus by so treating the esters of formula XXVI the corresponding compounds of formula XXIX can be prepared. Also preferably the ester function is hydrolyzed prior to the above described 9-position oxidation step.

The 10,11'ketal group can be removed, as previously described, by acid hydrolysis with a weak acid using extended reaction times or higher temperatures.

In an alternative process, the 10 substituted $PGF_1$ and $PGE_1$ derivatives of the present invention, unsubstituted and saturated at C-5, 6 can be obtained from the intermediate compounds of formula XXI, i.e., the $3',4'$-ketals of $7[(2'\alpha$-tetrahydropyranyloxy-$3'\alpha,4'\alpha$-dihydroxy-$5'\beta$-benzyloxymethyl)cyclopent- $1'\alpha$-yl]-hept-5-enoic acid alkyl ester and the $3',4'$-ketals of $7[(2'\alpha$-tetrahydropyranyloxy-$3'\alpha,4'\alpha$-dihydroxy-$5'\beta$-methoxymethyl)-cyclopent-$1'\alpha$-yl]-hept-5-enoic acid alkyl ester, which by catalytic hydrogenation of the C-5, 6 double bond. In the case of the 5'-benzyloxymethyl compounds the benzyloxymethyl group is simultaneously hydrogenolyzed. The saturated hydroxymethyl product (unsubstituted at C-5, 6) is then submitted to the reactions described above for the 5,6-methylene(halomethylene) compounds (i.e., oxidation, Wittig reaction, zinc borohydride reduction, separation of isomers, protection and hydrolysis of the protecting groups, and optional oxidation of the hydroxyl group at C-9).

The hydroxyl groups in the compounds of the invention can be esterified in a conventional manner to produce mono-, di-, tri- or tetraesters or mono-, di-, tri- or tetraethers, depending upon the particular prostaglandin derivative. For example, esterification can be accomplished by reaction of the hydroxylated compound with the desired carboxylic acid anhydride or chloride in pyridine solution.

Etherification of the hydroxy group can also be carried out by conventional techniques. For example by reaction with dihydropyran, dihydrofuran or 4-methoxy-5,6-dihydro-2H-pyran in an inert solvent such as, for example, benzene and in the presence of an acid catalyst (e.g., p-toluenesulfonic acid) produces the tetrahydropyran-2′-yloxy, tetrahydrofuran-2′-yloxy or 4′-methoxytetrahydropyran-4′-yloxy derivatives, respectively. Methyl, ethyl, and cyclopentyl ethers can, for example, be prepared by reaction of the hydroxylated compound with sodium hydride and methyl iodide, ethyl iodide, and cyclopentyl bromide, respectively.

Although the esterification or etherification reactions are usually effected using an excess of the esterifying or etherifying agents, it is preferable to use at least one molar equivalent of said reagents per hydroxyl group present in the starting compound.

The alkyl esters of the carboxy acid function can be prepared by treatment of the free acid with an excess of a diazoalkane such as diazomethane, diazoethane or diazopropane in ether or methylene chloride solution, in a conventional manner.

The salt derivatives of the prostanoic acids of the present invention can be prepared by treating the corresponding free acids with about one molar equivalent of a pharmaceutically acceptable base per molar equivalent of free acid. Suitable pharmaceutically acceptable bases include, for example, sodium hydroxide, potassium hydroxide, ammonium hydroxide, calcium hydroxide, trimethylamine, triethylamine, tripropylamine, β-(dimethylamino)ethanol, β-(diethylamino)ethanol, arginine, lysine, caffeine, procaine or the like. Typically the reaction is conducted in an aqueous solution, alone or in combination with an inert, water miscible organic solvent, at a temperature of about from 0° to 30°C, preferably at room temperature. Typical inert, water miscible organic solvents include methanol, ethanol, isopropanol, butanol, dioxane or tetrahydrofuran. When divalent metal salts are prepared, such as the calcium salts or magnesium salts, the free acid starting material is treated with at least one half molar equivalent of the pharmaceutically acceptable base.

The amide or carbonylamino, including the N-heterocyclic derivatives, derivatives of the invention can be prepared by treating the corresponding 1-position free acids of formulas A, B, C or D, of the invention, with ammonia or the desired substituted amine or N-heterocycle. Typically this treatment is conducted under aqueous conditions at temperatures in the range of about from 15° to 30°C for about 2 to 10 hours. Suitable amines and N-heterocycles include, for example, methylamine, ethylamine, isopropylamine, phenylethylamine, p-methylbenzyl, morpholine, pyrrolidine and piperidine. Where solubility problems are encountered, it is preferable to use a suitable inert organic solvent such as, for example, methanol, ethanol, pyridine and the like.

In conducting the aforedescribed processes, it is generally preferred to separate or isolate the respective products of each reaction step prior to their use as starting materials in subsequent steps. Illustrative non-limiting separation and isolation procedures can be had by reference to the appropriate Example set forth herein below. Also where pure optical isomer products are desired, such products can be obtained by the use of pure optical isomer starting materials or by resolution of the racemic product (or starting materials) according to conventional procedures such as, for example, described by Cerey et al, J. Am. Chem. Soc., 92, 397 (1970).

Also although the above processes, for purposes of simplicity, have been described with respect to tetrahydropyran and acetate protecting groups, other conventional suitable ether and ester protecting groups could, of course, also be used.

The starting materials used in the above described process, i.e., (2′α-hydroxy-4′α-acetoxy-3′β-iodo-5′β-benzyloxymethylcyclopent-1′α-yl)-acetic acid 1,2′-lactone and (2′α-hydroxy- 4′α-acetoxy-3′β-iodo-5′β-methoxymethylcyclopent-1′α-yl)-acetic acid 1′,2′-lactone are known compounds and can be obtained from known sources or prepared according to known procedures such as, for example, described by E. J. Corey et al, in J. Am. Chem. Soc., 91, 5675 (1969); J. Am. Chem. Soc., 92, 1397 (1970); J. Am. Chem. Soc., 93, 1489, 1490 and 1491 (1971) and references cited herein.

The preparation of these starting compounds can be illustrated as follows:

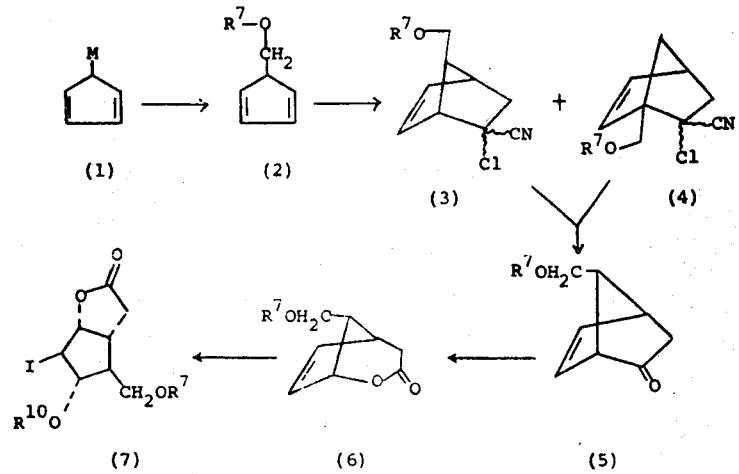

wherein $R^7$ have the above-indicated meaning; $R^{10}$ represents hydrogen or acetyl; and M represents sodium or thallium.

Briefly, this method comprises the reaction of cyclopentadienyl sodium or cyclopentadienyl thallium (1), obtained by reaction of cyclopentadiene with sodium hydride or lithium hydride aqueous thallous sulfate in the presence of potassium hydroxide (E. J. Corey et al, J. Am. Chem. Soc., 93, 1489 (1971), with a slight excess of chloromethyl methyl ether or chloromethyl benzylether in tetrahydrofuran at approximately −55°C, to yield respectively the 5-methoxymethyl-1,3-cyclopentadiene 2, ($R^7$ = methyl) or 5-benzyloxymethyl-1,3-cyclopentadiene 2 ($R^7$ = benzyl) which are subjected to the Diels Alder reaction with an excess (about 5 molar equivalents) of 2-chloroacrylonitrile in the presence of cupric fluoroborate as catalyst to yield a mixture of the endo-exo cyano nitriles of formulas (3) and (4) ($R^7$ = methyl or benzyl, respectively). This mixture of stereoisomeric nitriles is treated with potassium hydroxide in dimethylsulfoxide to yield the anti-bicyclic ketones of formula (5), i.e., 7-syn-methoxymethyl-2-norbornen-5-one ($R^7$ = methyl) or 7-syn-benzyloxymethyl-2-norbornen-5-one ($R^7$ = benzyl) respectively, which upon reaction with a slight molar excess of m-chloroperbenzoic acid in methylene chloride in the presence of sodium bicarbonate resulted in selective Baeyer-Villiger oxidation to form the corresponding lactone (6), i.e., 2-oxa-3-oxo-$\Delta^5$-8-syn-methoxymethylbicyclo(3,2,1) octane ($R^7$ = methyl), and 2-oxa-3-oxo-$\Delta^5$-8-syn-benzyloxymethylbicyclo (3,2,1) octane ($R^7$ = benzyl). Saponification of the foregoing lactones of formula (6) with 2.5 equivalents of sodium hydroxide in aqueous methanol, followed by neutralization with carbon dioxide and treatment with 2.5 equivalents of aqueous potassium triiodide solution at 0°–5°C produce the respective hydroxy-iodolactones of formula (7), namely (2′α,4′α-dihydroxy-3′β-iodo-5′β-benzyloxymethylcyclopent-1′α-yl)-acetic acid 1,2′-lactone ($R^7$ = methyl, $R^{10}$ = H) and (2′α,4′α-dihydroxy-3′β-iodo-5′β-methoxymethylcyclopent-1′β-yl)-acetic acid 1′,2′-lactone ($R^7$ = benzyl, $R^{10}$ = H), which can then be esterified with acetic anhydride in pyridine, under conventional conditions to yield the corresponding acetoxy compounds (7, $R^{10}$ = acetyl).

The compounds and salts of the invention exhibit prostaglandin-like biological activities and thus are useful in the treatment of mammals where the use of prostaglandins are indicated. The compounds and salts of the invention are bronchodilators and thus are useful in treating mammals for bronchial spasm or wherever strong bronchodilators are indicated. The compounds and salts are also useful in controlling or palliating hypertension in mammals and further exhibit central nervous system depressant activity, in mammals, and are useful as sedatives. In addition, the compounds are useful for inducing labor, in pregnancy, and for inducing menses to correct or reduce menstrual abnormalities.

The compounds and/or salts, of the invention, can be administered in a wide variety of dosage forms, either alone or in combination with other pharmaceutically compatible medicaments, in the form of pharmaceutical compositions suited for oral or parenteral administration or inhalation in the case of bronchodilators. The compounds are typically administered as pharmaceutical compositions consisting essentially of the compounds and/or salts, of the invention, and a pharmaceutical carrier. The pharmaceutical carrier can be either a solid material, liquid, or aerosol, in which the compound and/or salt is dissolved, dispersed or suspended, and can optionally contain samll amounts of preservatives and/or pH-buffering agents. Suitable preservatives which can be used include, for example, benzel alcohol and the like. Suitable buffering agents include, for example, sodium acetate and pharmaceutical phosphate salts and the like.

The liquid compositions can, for example, be in the form of solutions, emulsions, suspensions, syrups, or elixirs. The solid compositions can take the form of tablets, powders, capsules, pills or the like, preferably in unit dosage forms for simple administration or precise dosages. Suitable solid carriers include, for example, pharmaceutical grades of starch, lactose, sodium saccarin, talcum, sodium bisulfite and the like.

For inhalation administration, the compounds and/or salts can, for example, be administered as an aerosol comprising the compounds or salts in an inert propellant together with a co-solvent (e.g., ethanol) together with optional preservatives and buffering agents. Additional general information concerning the inhalation administration of aerosols can be had by reference to U.S. Pats. 2,868,691 and 3,095,355.

The compounds of this invention are typically administered in dosages of about from 0.1 to 10 mg. per kg. of body weight. The precise effective dosage will, of course, vary depending upon the mode of administration, condition being treated, and host.

A further understanding of the invention can be had from the following non-limiting Preparations and Examples. Also as used herein above and below unless expressly stated to the contrary, all temperatures and temperature ranges refer to the Centigrade system and the terms ambient or room temperature refers to about 20°C. The term percent or (%) refers to weight percent. The term molar equivalent (m. equiv.) refers to a quantity of reagent equal in moles to the moles of the immediately preceding reactant recited in the preparations and examples. Also unless expressly stated to the contrary, racemic mixtures are used as starting materials and correspondingly racemic mixtures are obtained as products and where necessary, preparations and examples are repeated for subsequent preparations and examples. The abbreviation t.l.c. refers to thin-layer chromatography.

PREPARATION 1

A. To a stirred solution of 125 g. of thallium sulfate and 50 g. of potassium hydroxide in 750 ml. of water are added, under an atmosphere of argon, 43 ml. of freshly distilled cyclopentadiene and the mixture is vigorously stirred for 10 minutes; the yellow precipitate formed is filtered off, washed with ice water, methanol and ether, to yield 132 g. of cyclopentadienylthallium.

B. A mixture of 216.28 g. of benzyl alcohol, 61.44 g. of paraformaldehyde, 481.6 g. of anhydrous magnesium sulfate and 1200 ml. of methylene chloride is cooled to a temperature of between −50° to −55°C in a dry ice-acetonitrile bath, and the stirred cold solution is saturated with an anhydrous hydrogen chloride gas. The reaction mixture is kept at −50° to −55°C for 10 minutes further, and then the excess of hydrogen chloride is eliminated by passing a stream of nitrogen during 30 minutes. The reaction mixture is filtered and the solid material washed well with pentane, and the combined filtrates are evaporated to dryness at a temperature below 30°C, to produce an oil which is distilled under reduced pressure to yield chloromethyl benzyl ether.

C. A suspension of 132 g. of cylopentadienylthallium in 200 ml. of anhydrous ether is cooled to −20°C in a dry ice-carbon tetrachloride bath. To the cooled mixture is added under stirring and under an argon atmosphere, in a 15 minute period, 90 g. or chloromethyl benzyl ether. The reaction mixture is stirred for 3½ hours at −20°C, it is then filtered in a filtration flask previously cooled to −78°C and the solid precipitate washed with cold pentane (−78°C).

The filtered solution is immediately added to a mixture of 216 g. of anhydrous α-chloroacrylonitrile and 30 g. of anhydrous cupric fluoroborate, previously cooled to −78°C. The reaction mixture is evaporated to half its original volume at a temperature not higher than 0°C, and the concentrate is stirred at 0°C for 48 hours. The reaction mixture is then poured into 200 ml. of saturated sodium chloride solution and extracted three times with ether. The combined extracts are washed with saturated sodium bicarbonate solution (2 × 200 ml.) and saturated sodium chloride solution (2 × 200 ml.), dried over magnesium sulfate and evaporated to dryness under reduced pressure. The resulting residue is purified by filtration through 100 g. of silica gel using benzene as eluant, thus obtaining the pure 2-chloro-2-cyano-$\Delta^5$-7-syn-benzyloxymethyl-bicyclo-(2.2.1)-heptane.

PREPARATION 2

To a well-stirred slurry of 74.1 g. of cyclopentadienyl-thallium in 100 ml. of anhydrous ether cooled to −20° to −22°C (internal temperature) in a dry-ice carbon tetrachloride bath under an argon atmosphere, is added dropwise, in a 15 minute period, 20.13 g. of chloromethyl methyl ether and the slurry is stirred at −20° to −22° for 7 hours. The reaction mixture is then filtered into a precooled (−70°, dry-ice-acetone) flask and the residue of thallium chloride washed with three 100 ml. portions of cold (−70°) ether. The combined filtrate is added dropwise from a dropping funnel with a dry-ice jacket to a suspension of 29.65 g. of cupric tetrafluoroborate in 87.5 g. of anhydrous '-chloroacrylonitrile maintained at 0°C. When the addition is complete, the mixture is stirred at 0°C in the dark for 18 hours.

100 Ml. of saturated sodium chloride solution is then added and the reaction mixture extracted with ether. The ether extracts are successively washed with saturated sodium bicarbonate (2 × 100 ml.) and sodium chloride (2 × 100 ml.), and dried over magnesium sulfate. Evaporation under reduced pressure at room temperature gives 2-chloro-2-cyano-$\Delta^5$-7-syn-methoxymethylbicyclo-(2.2.1)-heptane as a clear pale yellow oil.

PREPARATION 3

To a stirred solution of 100 g. of 2-chloro-2-cyano-$\Delta^5$-7-syn-benzyloxymethylbicyclo-(2.2.1)-heptane in 368 ml. of dimethylsulfoxide is added dropwise, in a 15 minute period and under an argon atmosphere, a hot solution of 105.2 g. of potassium hydroxide in 52.6 ml. of water. The reaction mixture is stirred for 28 hours at room temperature, diluted to twice its volume with ice water and extracted several times with ether. The combined organic extract is washed twice with saturated sodium carbonate solution, dried over magnesium sulfate and evaporated to dryness. The residue is purified by distillation under high vacuum (0.6 mm) to yield 7syn-benzyl-oxymethyl-2-norbornen-5-one, which is further purified by thin-layer chromatography.

By the same procedure but using 2-chloro-2-cyano-$\Delta^5$-7-syn-methoxymethylbicyclo-(2.2.1)-heptane in lieu of 2-chloro-2-cyano-$\Delta^5$-7-syn-benzyloxymethylbicyclo-(2.2.1)-heptane, there is obtained 7-syn-methoxy-methyl-2-norbornen-5-one.

PREPARATION 4

To a suspension of 55 g. of m-chloroperbenzoic acid and 43.5 g. of sodium bicarbonate in 570 ml. of anhydrous methylene chloride are added 57 g. of 7-syn-benzyloxymethyl-2-norbornen-5-one, in a 15 minute period and under stirring, maintaining the temperature at about 25° C. The reaction mixture is stirred for 3 hours further, and diluted with methylene chloride. The resulting mixture is vigorously stirred with 470 ml. of saturated aqueous sodium sulfite solution, the organic layer is separated and washed with saturated sodium sulfite solution. The aqueous phase is extracted with methylene chloride and the combined organic extracts are dried over magnesium sulfate and evaporated to dryness under reduced pressure yielding 2-oxa-3-oxo-$\Delta^5$-8-syn-benzyloxymethylbicyclo-(3.2.1)-octane.

By the same procedure but using 7-syn-methoxymethyl-2-norbornen-5-one in place of 7-syn-benzyloxymethyl-2-norbornen-5-one there is obtained 2-oxa-3-oxo-$\Delta^5$-8-syn-methoxymethyl-bicyclo-(3.2.1)-octane.

PREPARATION 5

To a solution of 60 g. of 2-oxa-3-oxo-$\Delta^5$-8-syn-benzyloxymethylbicyclo-(3.2.1)-octane in 70 ml. of methanol is added, at 0°C, a solution of 30 g. of sodium hydroxide in 247 ml. of water, and the resulting mixture is stirred at room temperature for 3 hours. The methanol is then evaporated under vacuo at a temperature below 30°C, cooled to 0°C and extracted with ether to eliminate the neutral products. The aqueous phase is neutralized with carbon dioxide and immediately treated with a solution of 188.1 g. of iodine and 369 g. of potassium iodide in 275 ml. of water. The reaction mixture is stirred for 48 hours at 0°C and diluted with sodium sulphite solution until complete decoloration. It is then saturated with sodium potassium tartrate and extracted with methylene chloride. The organic extracts are dried over magnesium sulfate and evaporated to dryness under reduced pressure. The oily residue is crystallized from ether-methylene chloride, to yield (2'α,4'α-dihydroxy-3'β-iodo-5'β-benzyloxymethylcyclopent-1'α-yl)-acetic acid 1,2'-lactone.

By the same procedure, 2-oxa-3-oxo-$\Delta^5$-8-syn-methoxymethylbicyclo-(3.2.1)-octane is converted into (2'α,4'α-dihydroxy-3'β-iodo-5'β-methoxymethylcyclopent-1'α-yl)-acetic acid 1,2'-lactone.

PREPARATION 6

A mixture of 2.5 g. of (2'α,4'α-dihydroxy-3'β-iodo-5'β-benzyloxymethylcyclopent-1'α-yl)-acetic acid 1,2'-lactone, 2.5 ml. of pyridine and 5 ml. of acetic anhydride is kept at room temperature for 30 minutes. The solvents are then evaporated under reduced pressure, and the residue crystallized from ether, to yield (2'α-hydroxy-4'α-acetoxy-3'β-iodo-5'β-benzyloxymethylcyclopent-1'α-yl)-acetic acid 1,2'-lactone.

In a similar manner (2'α,4'α-dihydroxy-3'β-iodo-5'β-methoxymethylcyclopent-1'α-yl)-acetic acid 1,2'-lactone is converted into the corresponding 4'-acetoxy derivative.

EXAMPLE 1

To a solution of 2 g. of (2'α-hydroxy-4'α-acetoxy-3'β-iodo-5'β-benzyloxymethylcyclopent-1'α-yl)-acetic acid 1,2'-lactone in 20 ml. of acetic acid are added 1.4 ml. of water and 2 g. of silver acetate, and the mixture is refluxed for 2 hours. The silver iodide is separated by filtration and washed several times with ethyl acetate. The combined organic filtrates are evaporated to dryness under reduced pressure, the residue is diluted with ethyl acetate and the insoluble material filtered off. Upon evaporation of the filtrate under vacuo there is produced a mixture of (4'α-acetoxy-2'α,3'α-dihydroxy-5'β-benzyloxymethylcyclopent-1'α-yl)-acetic acid 1,2'-lactone and (3'α-acetoxy-2'α,4'α-dihydroxy-5'β-benzyloxymethylcyclopent-1'α-yl)-acetic acid 1,2'-lactone.

In a similar manner but using (4'α-acetoxy-2'α-hydroxy-3'β-iodo-5'β-methoxymethylcyclopent-1'α-yl)-acetic acid 1,2'-lactone as starting material there is obtained a mixture of (4'α-acetoxy-2'α,3'α-dihydroxy-5'β-methoxymethylcyclopent-1'α-yl)-acetic acid 1,2'-lactone and (3'α-acetoxy-2'α,4'α-dihydroxy-5'β-methoxymethylcyclopent-1'α-yl)-acetic acid 1,2'-lactone.

EXAMPLE 2

A solution of 640 mg. of the mixture of (4'α-acetoxy-2'α,3'α-dihydroxy-5'β-benzyloxymethylcyclopent-1'α-yl)-acetic acid 1,2'-lactone and (3'α-acetoxy-2'α,4'α-dihydroxy-5'β-benzyloxymethylcyclopent-1'α-yl)-acetic acid 1,2'-lactone in 20 ml of methanol is treated with 592 mg. of anhydrous potassium carbonate, and the reaction mixture stirred for 2½ hours at room temperature. It is then cooled to 0°C and neutralized with 10% aqueous hydrochloric acid, until a pH of 2–3 is obtained. Ethyl acetate is added and the organic solution washed with water to neutral, dried over magnesium sulfate and evaporated to dryness under vacuo, to yield 500 mg. of (2'α,3'α,4'α-trihydroxy-5'β-benzyloxymethylcyclopent-1'α-yl)-acetic acid 1,2'-lactone, which is further purified by crystallization from ethyl acetate.

Likewise, starting from the mixture of (4'α-acetoxy-2'α,3'α-dihydroxy-5'β-methoxymethylcyclopent-1'α-yl)-acetic acid 1,2'-lactone and (3'α-acetoxy-2'α,4'α-dihydroxy-5'β-methoxymethylcyclopent-1'α-yl)-acetic acid 1,2'-lactone, there is produced (2'α,3'α,4'α-trihydroxy-5'β-methoxymethylcyclopent-1'α-yl)-acetic acid 1,2'-lactone.

EXAMPLE 3

To a solution of 4 g. of (2'α,3'α,4'α-trihydroxy-5'β-benzyloxymethylcyclopent-1'α-yl)-acetic acid 1,2'-lactone in 20 ml. of anhydrous acetone and 5 ml. of 2,2-dimethoxypropane are added 10 mg. of p-toluenesulfonic acid, and the reaction mixture is kept at room temperature for 2.5 hours. A few drops of pyridine are then added, and the solvents eliminated under reduced pressure. The residue is crystallized from ethyl acetate-hexane, to yield (2'α-hydroxy-3'α,4'α-isopropylidenedioxy-5'β-benzyloxymethylcyclopent-1'α-yl)-acetic acid 1,2'-lactone which is then further purified by thin-layer chromatography.

By the same method (2'α,3'α,4'α-trihydroxy-5'β-methoxymethylcyclopent-1'α-yl)-acetic acid 1,2'-lactone is converted into (2'α-hydroxy-3'α,4'α-isopropylidenedioxy-5'β-methoxymethylcyclopent-1'α-yl)-acetic acid 1,2'-lactone.

EXAMPLE 4

To a prehydrogenated suspension of 90 mg. of 10% palladium charcoal catalyst in 10 ml. of acetone (distilled first from potassium permanganate and then from chromium trioxide) are added 954 mg. of (2'α-hydroxy-3'α,4'α-isopropylidenedioxy-5'β-benzyloxymethylcyclopent-1'α-yl)-acetic acid 1,2'-lactone and 2 drops of perchloric acid, and the mixture is stirred under hydrogen atmosphere until the absorption of hydrogen ceases. The catalyst is then separated by filtration and washed with ether. To the combined organic solutions are added 4 drops of pyridine and the mixture is evaporated to dryness under reduced pressure. Crystallization of the residue from chloroform yields (2'α-hydroxy-3'α,4'α-isopropylidenedioxy-5'β-hydroxymethylcyclopent-1'α-yl)-acetic acid 1,2'-lactone which is then further purified by thin-layer chromatography.

EXAMPLE 5

A stirred solution of 15 g. of (2'α-hydroxy-3'α,4'α-isopropylidenedioxy-5'β-methoxymethylcyclopent-1'α-yl)-acetic acid 1,2'-lactone in 190 ml. of anhydrous methylene chloride is cooled to −79°C in a dry ice-acetone bath and treated with 25 ml. of boron tribromide. The stirred mixture is allowed to warm rapidly to 0°C and kept at this temperature for 50 minutes. The resultant solution is diluted with 270 ml. of ether while maintaining the reaction mixture of 0°C. It is then poured into a vigorously stirred slurry of 95 g. of sodium bicarbonate in 500 ml. of a saturated solution of sodium potassium tartrate; the organic layer is separated and the aqueous phase extracted with methylene chloride. The combined organic extracts are dried over magnesium sulfate and evaporated to dryness under reduced pressure. The residue is purified by crystallization from chloroform to afford (2'α-hydroxy-3'α,4'α-isopropylidenedioxy-5'β-hydroxymethylcyclopent-1'αyl)-acetic acid 1,2'-lactone.

EXAMPLE 6

A. Preparation of chromium trioxide-dipyridine complex.

To 600 ml. of anhydrous pyridine are added under stirring at a temperature of between 10° and 15° C and in a 15 minute period, 80 g. of chromium trioxide, which has been previously dried at 110°C for 48 hours. The reaction mixture is stirred for 30 minutes further and rapidly filtered in the absence of moisture. The solid is washed with anhydrous pentane, dried and stored in a desiccator.

B. To a suspension of 11 g. of diatomaceous earth (dried for 24 hours at 105° C) and 5.16 g. of the chromium trioxidedipyridine complex in 52 ml. of anhydrous methylene chloride, cooled to −5° C are added under stirring 6.1 g. of (2'α-hydroxy-3'α,4'α-isopropylidenedioxy-5'β-hydroxymethylcyclopent-1'α-yl)-acetic acid 1,2'-lactone and the mixture is stirred for 10 minutes further, maintaining the temperature between −5° and 0° C; 16 g. of sodium bisulfite monohydrate are then added and the mixture is stirred for an additional 10 minute period, filtered through magnesium sulfate and the solids washed with methylene chloride, receiving the filtrate in a flask cooled to −60° C in a dry-ice acetone bath. The combined filtrates are evaporated to dryness under reduced pressure, at a temperature controlled below 0° C, obtaining (2'α-hydroxy-3'α,4'α-isopropylidenedioxy-5'β -formylcyclopent-1'α-yl)-acetic acid 1,2'-lactone.

EXAMPLE 7

A. Preparation of dimethyl-2-oxoheptylphosphonate.

A solution of 100 g. of dimethyl methylphosphonate in 670 ml. of anhydrous tetrahydrofuran is cooled to −78° C under an argon atmosphere. To the cold solution is added dropwise under stirring and under argon atmosphere, 495 ml. of a 0.1M solution of N-butyllithium in tetrahydrofuran, maintaining the temperature at −70° C. When the addition is complete the reaction mixture is maintained under the same conditions for 10 additional minutes, a solution of 48 ml. of methyl caproate dissolved in 187 ml. of tetrahydrofuran is then carefully added, maintaining the temperature at −78° C. The reaction mixture is stirred at −78° C for 2 hours followed by stirring for 4 hours at room temperature. The excess base is neutralized with acetic acid and the solvent is evaporated under high vacuo. The residue is dissolved in ethyl ether-water (1:1, 950 ml. each), the ethereal phase is separated, washed with water and dried over magnesium sulfate. The ether is evaporated and the residue is purified by vacuum distillation, yielding pure dimethyl-2-oxoheptyl phosphonate.

B. To a suspension of 135 mg. of sodium hydride (previously washed with pentane, under argon) in 40 ml. of dimethoxyethane freshly distilled from lithium aluminum hydride is added, under stirring and under an atmosphere of argon, a solution of 666 mg. of dimethyl-2-oxoheptylphosphonate in 15 ml. of dimethoxyethane. The reaction mixture is stirred for 30 minutes at room temperature and 530 mg. of (2'α-hydroxy-3'α,4'α-isopropylidenedioxy-5'β-formylcyclopent-1'α-yl)-acetic acid 1,2'-lactone are added. The reaction mixture is stirred at room temperature for an additional 2 hours and then carefully neutralized with acetic acid (to pH 7) and evaporated to dryness under reduced pressure at a temperature controlled below 30° C. The solid residue is purified by chromatography on alkaline alumina, using methylene chloride-methanol (97:3) as eluant, yielding [2'α-hydroxy-3'α,4'α-isopropylidenedioxy-5'β-(3''-oxo-oct-1''(t)-en-1''-yl)-cyclopent-1'α-yl]-acetic acid 1,2'-lactone of 2-oxoheptyl phosphonate.

EXAMPLE 8

Four grams of [2'α-hydroxy-3'α,4'α-isopropylidenedioxy-5'β-(3''-oxooct-1''(t)-en-1''yl)-cyclopent-1'α-yl]-acetic acid 1,2'-lactone is dissolved in 48 ml. of dimethoxyethane freshly distilled from lithium aluminum hydride. To the stirred solution are added 12 ml. of zinc borohydride reagent in anhydrous dimethoxyethane. The reaction mixture is stirred for an additional hour at room temperature, and treated with a saturated solution of sodium bitartrate until the evolution of gas ceases. It is then diluted with methylene chloride, dried over magnesium sulfate and evaporated to dryness under vacuo at a temperature below 30° C, to yield [2'α-hydroxy-3'α,4'α-isopropylidenedioxy-5'β-(3''α-hydroxy-oct-1''(t)-ene)-cyclopent-1'α-yl]-acetic acid 1,2'-lactone in mixture with the 3''β-hydroxy isomer.

This mixture is separated by thin-layer chromatography using a mixture of methylene chloride-methanol 95:5 as eluant.

The zinc borohydride reagent is prepared from 0.025 mole of fused zinc chloride, 0.050 mole of sodium borohydride in 50 ml. of dimethoxyethane, stirring the mixture for 16 hours and filtering the insoluble material under argon atmosphere.

EXAMPLE 9

To a solution of 1.4 g. of [2'α-hydroxy-3'α,4'α-isopropylidenedioxy)-5'β-(3''β-hydroxyoct-1''(t)-en-1''-yl)-cyclopent-1'α-yl]-acetic acid 1,2'-lactone in 85 ml. of anhydrous tetrahydrofuran is added 3.2 g. of manganese dioxide, and the reaction mixture is stirred for 30 minutes at room temperature; 3.2 g. portions of manganese dioxide are added at 30 minute intervals, during 3½ hours. The manganese dioxide is separated by filtration and washed with hot acetone. The combined organic filtrates are evaporated to dryness under reduced pressure, and the residue is purified by thin-layer chromatography thus obtaining the pure [2'α-hydroxy-3'α,4'α-isopropylidenedioxy-5'β-(3''-oxooct-1''(t)-en-1''-yl)-cyclopent-1'α-yl]-acetic acid 1,2'-lactone.

EXAMPLE 10

To a solution of 4 g. of [2'α-hydroxy-3'α,4'α-isopropylidenedioxy)-5'β-(3''β-hydroxyoct-1''(t)-en-1''-yl)-cyclopent-1'α-yl]-acetic acid 1,2'-lactone in 40 ml. of methylene chloride are added 2.5 ml. of freshly distilled dihydropyran and 40 mg. of anhydrous p-toluenesulfonic acid. The reaction mixture is stirred for 30 minutes, at room temperature, a few drops of pyridine are added and diluted with ether. The ethereal solution is washed with 100 ml. of 50% aqueous sodium chloride solution and then with saturated sodium chloride solution. The organic phase is separated, dried over mangesium sulfate and evaporated to dryness under reduced pressure, at approximately 0° C. The oily residue is purified by thin-layer chromatography using hexane-ethyl acetate 7:3 as eluant, to produce the pure [2'α-hydroxy-3'α,4'α-isopropylidenedioxy-5'β-(3''α-tetrahydropyranyloxyoct-1''(t)-en-1''-yl)-cyclopent-1'α-yl]-acetic acid 1,2' -lactone.

EXAMPLE 11

One hundred and fifty milligrams of [2'α-hydroxy-3'α,4'α-isopropylidenedioxy-5'β-(3''α-tetrahydropyranyloxyoct-1''(t)-en-1''-yl)-cyclopent-1'α-yl]-acetic acid 1,2'-lactone are dissolved in 3 ml. of anhydrous toluene. The solution is cooled to −60° C and to the cold solution is added a solution of 60 mg. of diisobutylaluminum hydride in 0.3 ml. of anhydrous toluene, stirring the reaction mixture for 15 minutes at −60° C. It is then diluted with methanol until the evolution of gas ceases, the mixture is stirred for 15 minutes further at room temperature and diluted with ether. The organic phase is then separated, washed with saturated sodium chloride solution, dried over magnesium sulfate and evaporated to dryness at about 0° C affording [2'α-hydroxy-3'α,4'α-isopropylidenedioxy-5'β-(3''α-tetrahydropyranyloxyoct-1''(t)-en-1''-yl)-cyclopent-1'α-yl]-acetaldehyde 1,2'-hemiacetal.

EXAMPLE 12

A stirred suspension of 440 mg. of sodium hydride in 5 ml. of anhydrous dimethylsulfoxide is heated to 80°C for half an hour under an argon atmosphere. 1.4 Ml. of the resulting solution is added to a solution of 380 mg. of dried 5-triphenylphosphoniopentanoic acid bromide in 0.8 ml. of anhydrous dimethylsulfoxide, under an argon atmosphere with stirring. After 5 minutes, 150 mg. of [2'α-hydroxy-3'α,4'α-isopropylidenedioxy-5'β-(3''α-tetrahydropyranyloxyoct-1''(t)-en-1''-yl)-cyclopent-1'α-yl]-acetaldehyde 1,2'-hemiacetal dissolved in 1 ml. of dimethylsulfoxide is added, and the reaction mixture is stirred at room temperature for 18 hours. The solvent is then evaporated under reduced pressure at a temperature below 35° C and the residue is dissolved in 10 ml. of water. The neutral products are extracted with ethyl acetate:ether (1:1) (4 × 4 ml.). The aqueous phase is acidified with saturated aqueous oxalic acid solution to pH 2, and extracted several times with a mixture of pentane: ethyl ether (1:1). The combined organic extracts are washed with saturated aqueous sodium chloride solution, dried over magnesium sulfate and evaporated to dryness at a temperature controlled below 20° C. The residue is purified by thin-layer chromatography using chloroform:methanol 9:1 as eluant, affording pure 9α-hydroxy-10α,11α-isopropylidenedioxy-15α-tetrahydropyranyloxyprosta-5,13-dienoic acid (10,11-acetonide-15-tetrahydropyranylether of 10α-hydroxy-PGF$_{2\alpha}$ ).

The 5-triphenylphosphoniopentanoic acid bromide used as reagent is prepared by refluxing a mixture of 9.5 g. of 5-bromopentanoic acid, 14.4 g. of triphenylphosphine and 100 ml. of acetonitrile for about 70 hours. The insoluble material is separated by filtration and the filtrate is concentrated to a small volume. The product is crystallized by addition of ether, and is further purified by two subsequent recrystallizations from acetonitrile-ether.

EXAMPLE 13

A solution of 100 mg. of 9α-hydroxy-10α,11α-isopropylidenedioxy-15α-tetrahydropyranyloxyprosta-5,13-dienoic acid in 0.270 ml. of tetrahydrofuran is treated with 2.6 ml. of 65% aqueous acetic acid. The reaction mixture is stirred at 45° C for 4 hours, cooled to 0° C and evaporated to dryness under reduced pressure; the oily residue is purified by thin-layer chromatography using chloroform:methanol (9:1) as eluant, yielding pure 9α,15α-dihydroxy-10α,11α-isopropylidenedioxyprosta-5,13-dienoic acid.

In another experiment the reaction mixture is kept at room temperature for 18 hours, obtaining the same results.

EXAMPLE 14

To a solution of 100 mg. of 9α-hydroxy-10α,11α-isopropylidenedioxy-15α-tetrahydropyranyloxyprosta-5,13-dienoic acid in 10 ml. of methanol is added a solution of 50 mg. of oxalic acid in 1 ml. of water. The reaction mixture is maintained at room temperature for 1 hour, then diluted with water and extracted with methylene chloride. The organic extract is washed with aqueous sodium chloride solution, dried over magnesium sulfate and evaporated to dryness under reduced pressure. The resulting residue is purified by thin-layer chromatography using chloroform:methanol (9:1) as eluant, yielding the pure 9α,15α-dihydroxy-10α,11α-isopropylidenedioxyprosta-5,13-dienoic acid.

EXAMPLE 15

A solution of 100 mg. of 9α-hydroxy-10α,11α-isopropylidenedioxy-15α-tetrahydropyranyloxyprosta-5,13-dienoic acid in 3 ml. of acetone is cooled to −10° C and treated under an atmosphere of nitrogen and with stirring, with 0.1 ml. of an 8N solution of chromic acid (prepared by mixing 26 g. of chromium trioxide with 23 ml. of concentrated sulfuric acid and diluting with water to 100 ml.). After addition of the chromic acid, the reaction mixture is stirred for 25 minutes at −10° C. A few drops of methanol are then added to destroy the excess chromic acid and the mixture diluted with ethyl acetate. The solution is immediately washed 3 times with aqueous sodium chloride solution, dried over magnesium sulfate and evaporated to dryness under reduced pressure affording 9-keto-10α,11β-isopropylidenedioxy-15α-tetrahydropyranyloxyprosta-5,13-dienoic acid, which is then purified by thin-layer chromatography.

The tetrahydropyranyloxy moiety is then cleaved with acetic acid-water (65:35), in accordance with the method of Example 13 affording 9-keto-10α,11α-isopropylidenedioxy-15α-hydroxyprosta-5,13-dienoic acid (10,11-acetonide of 10α-hydroxy PGE$_2$).

EXAMPLE 16

To a solution of 100 mg. of 9α-hydroxy-10α,11α-isopropylidenedioxy-15α-tetrahydropyranyloxyprosta-5,13-dienoic acid in 0.3 ml. of tetrahydrofuran is added 0.3 ml. of 65% aqueous acetic acid. The reaction mixture is stirred at 45° C for 16 hours, then cooled to room temperature and evaporated to dryness under reduced pressure. Chromatography of the residue on a silica plate produces the pure 9α,10α,11α,15α-tetrahydroxyprosta-5,13-dienoic acid.

In a similar manner, 9-keto-10α,11α-isopropylidenedioxy-15α-tetrahydropyranyloxyprosta-5,13-dienoic acid is converted into 9-keto-10α,11α,15α-trihydroxyprosta-5,13-dienoic acid.

EXAMPLE 17

To a solution of 100 mg. of 9α,15α-dihydroxy-10α,11α-isopropylidenedioxyprosta-5,13-dienoic acid in 5 ml. of ether is added 1 ml. of an ethereal solution of diazomethane, and the reaction mixture is maintained at room temperature for 10 minutes. The solvents and excess reagent are eliminated by vacuum distillation and the residue is purified by thin-layer chromatography to afford 9α,15α-dihydroxy-10α,11α-isopropylidenedioxyprosta-5,13-dienoic acid methyl ester.

In a similar manner but using diazoethane in place of diazomethane, the ethyl ester of 9α,15α-dihydroxy-10α,11α-isopropylidenedioxyprosta-5,13-dienoic acid is obtained.

similarly, 9α,10α,11α,15α-tetrahydroxyprosta-5,13-dienoic acid; 9-keto-10α,11α-isopropylidenedioxy-15α-hydroxyprosta-5,13-dienoic acid; and 9-keto-10α,11α,15α-trihydroxyprosta-5,13-dienoic acid are converted into the corresponding methyl and ethyl esters.

EXAMPLE 18

A solution of 325 mg. of 9α,15α-dihydroxy-10α,11α-isopropylidenedioxyprosta-5,13-dienoic acid methyl ester in 20 ml. of 70% aqueous dimethylamine is maintained at room temperature for 96 hours. The reaction mixture is then treated dropwise with an ethereal solution of diazomethane until the color of the reagent persists in the mixture, the reaction mixture is stirred for 5 minutes and then evaporated to dryness under reduced pressure. The residue is purified by chromatography on Florisil; the fractions eluted with methylene chloride-ethyl acetate (60:40) correspond to recovered starting material and the fractions eluted with pure ethyl acetate afford the N,N-dimethylamide of 9α,15α-dihydroxy-10α,11α-isopropylidenedioxyprosta-5,13-dienoic acid.

In a similar manner but respectively using ammonia, methylamine, diethylamine and morpholine in place of dimethylamine, the following compounds are respectively prepared:

9α,15α-dihydroxy-10α,11α-isopropylidenedioxyprosta-5,13-dienoic acid amide;
9α,15α-dihydroxy-10α,11α-isopropylidenedioxyprosta-5,13-dienoic acid methylamide;
9α,15α-dihydroxy-10α,11α-isopropylidenedioxyprosta-5,13-dienoic acid diethylamide; and
9α,15α-dihydroxy-10α,11α-isopropylidenedioxyprosta-5,13-dienoic acid morpholineamide.

EXAMPLE 19

A suspension of 25 mg. of 5% palladium charcoal in 5 ml. of methanol is stirred in an atmosphere of hydrogen for 30 minutes. To the prehydrogenated catalyst suspension is added a solution of 100 mg. of 9α-hydroxy-10α,11α-isopropylidenedioxy-15α-tetrahydropyranyloxyprosta-5,13-dienoic acid in 10 ml. of methanol. The mixture is cooled to −15° to −20° C in a dry ice-acetone bath, and is then hydrogenated at this temperature and at atmospheric pressure. The progress of the reaction is followed by thin-layer chromatographic analysis of samples taken every ten minutes. The hydrogenation is interrupted as soon as the analysis indicates that the major product is the 5,6-dihydro-derivative, and that the completely saturated compound is beginning to form. The catalyst is then separated by filtration, washed with methanol, and the combined filtrates evaporated to dryness under reduced pressure. The residue is purified by thin-layer chromatography to yield the pure 9α-hydroxy-10α,11α-isopropylidenedioxy-15α-tetrahydropyranyloxyprost-13-enoic acid.

The product is divided into two equal portions and one portion is hydrolyzed with aqueous acetic acid, in accordance with the method of Example 13, affording 9α,15α-dihydroxy-10α,11α-isopropylidenedioxyprost-13-enoic acid (10,11-acetonide of 10α-hydroxy PGF$_{1\alpha}$).

By the same method, 9-keto-10α,11α-isopropylidenedioxy-15α-tetrahydropyranyloxyprosta-5,13-dienoic acid is converted into 9-keto-15α-hydroxy-10α,11α-isopropylidenedioxyprost-13-enoic acid (10,11-acetonide of 10α-hydroxy PGE$_1$).

The second product positions are then hydrolyzed for 16 hours, as described in Example 16, affording respectively 9α,10α,11α,15α-tetrahydroxyprost-13-enoic acid and 9-keto-10α,11α,15α-trihydroxyprost-13-enoic acid.

EXAMPLE 20

To a solution of 4 g. of (2'α,3'α,4'α-trihydroxy-5'β-benzyloxymethylcyclopent-1'α-yl)-acetic acid 1,2'-lactone in 15 ml. of anhydrous cyclohexanone and 5 ml. of 2,2-dimethoxypropane are added 10 mg. of p-toluenesulfonic acid, and the reaction mixture is kept at room temperature for 4 hours. A few drops of pyridine are then added, and the solvents eliminated under reduced pressure. The residue is crystallized from ethyl acetate-hexane, to yield the 3',4'-cyclohexanonide of (2'α,3'α,4'α-trihydroxy-5'β-benzyloxymethylcyclopent-1'α-yl)-acetic acid 1,2'-lactone which is then further purified by thin-layer chromatography.

The product cyclohexanonide derivative is then hydrogenlyzed in the presence of 10% palladium charcoal and perchloric acid in acetone solution in accordance with the method described in Example 4, affording the 3,4-cyclohexanonide of (2'α,3'α,4'α-trihydroxy-5'β-hydroxymethylcyclopent-1'α-yl)-acetic acid 1,2'-lactone.

This product is oxidized with chromium trioxide-dipyridine complex (Collins reagent) in accordance with the method of Example 6 to yield the 3',4'-cyclohexanonide of (2'α,3'α,4'α-trihydroxy-5'β-formylcyclopent-1'α-yl)-acetic acid 1,2'-lactone.

EXAMPLE 21

To a suspension of 135 mg. of sodium hydride (previously washed with pentane, under argon) in 40 ml. of dimethoxyethane freshly distilled from lithium aluminum hydride is added, under stirring and under an atmosphere of argon, a solution of 666 mg. of dimethyl-2-oxoheptylphosphonate in 15 ml. of dimethoxyethane. The reaction mixture is stirred for 30 minutes at room temperature and 600 mg. of the 3',4'-cyclohexanonide of (2'α,3'α,4'α-trihydroxy-5'β-formylcyclopent-1'α-yl)-acetic acid 1,2'-lactone are added. The reaction mixture is stirred at room temperature for 2 hours further, it is then carefully neutralized with acetic acid (to pH 7) and evaporated to dryness under reduced pressure at a temperature below 30° C. The solid residue is purified by chromatography on alkaline alumina, using methylene chloride-methanol (97:3) as eluant, to obtain the 3',4'-cyclohexanonide of [2'α,3'α,4'α-trihydroxy-5'β-(oxt-1''(t)-en-3''-on-1'' -yl)-cyclopent-1'α-yl]-acetic acid 1,2'-lactone and a small amount of 2-oxoheptyl phosphonate.

Four grams of the 3',4'-cyclohexanonide of [2'α,3'α,4'α-trihydroxy-5'β-(3-oxo-oct-1(t)-en-1-yl)-cyclopent-1'α-yl]-acetic acid 1,2'-lactone are dissolved in 48 ml. of dimethoxyethane freshly distilled from lithium aluminum hydride. To the stirred solution are added 12 ml. of zinc borohydride reagent (obtained as described in Example 8). The reaction mixture is stirred for an additional hour at room temperature and treated with a saturated solution of sodium bitartrate until the evolution of gas ceases. It is then diluted with methylene chloride, dried over magnesium sulfate and evaporated to dryness under vacuo at a temperature below 30° C, to yield the 3',4'-cyclohexanonide of [2'α,3'α,4'α-trihydroxy-5'β-(3''α-hydroxyoct-1''(t)-en-1''-yl)-cyclopent-1'α-yl]-acetic acid 1,2'-lactone in mixture with the 3''β-hydroxy isomer.

This oily mixture is separated by thin-layer chromatography using a mixture of methylene chloride-methanol 95:5 al eluant.

EXAMPLE 22

By following the method of Example 10, 2 g. of the 3',4'-cyclohexanonide of [2'α,3'α,4'α-trihydroxy-5'β-(3''α-hydroxyoct-1''(t)-en-1''-yl)-cyclopent-1'α-yl]- acetic acid 1,2'-lactone is etherfied with dihydropyran in methylene chloride solution and in the presence of p-toluenesulfonic acid, to afford the 3',4'-cyclohexanonide of [2'α,3'α,4'α-trihydroxy-5'β-(3''α-tetrahydropyranyloxyoct-1''(t)-en-1''-yl)-cyclopent-1'α-yl]-acetic acid 1,2'-lactone, which upon reaction with diisobutylaluminum hydride in toluene solution, in accordance with the method of Example 11 produces the 3',4'-cyclohexanonide of [2'α,3'α,4'α-trihydroxy-5'β-(3''α-tetrahydropyanyloxyoct-1''(t)-en-1''-yl)-cyclopent-1'α-yl]-acetaldehyde 1,2'-hemiacetal.

EXAMPLE 23

A stirred suspension of 440 mg. of sodium hydride (previously washed with hexane) in 5 ml. of anhydrous dimethylsulfoxide is heated to 80° C for half an hour under an argon atmosphere. Five milliliters of the resulting solution is added a solution of 2.27 g. of dried 5-triphenylphosphoniopentanoic acid bromide in 4.3 ml. of anhydrous dimethylsulfoxide, under an argon atmosphere and under stirring. The reaction mixture is stirred for 5 minutes; 700 mg. of the 3',4'-cyclohexanonide of [2'α,3'α,4'α-trihydroxy-5'β-(3''α-tetrahydropyranyloxyoct-1''(t)-en-1''-yl)-cyclopent-1'α-yl]-acetaldehyde 1,2'-hemiacetal, dissolved in 3 ml. of dimethylsulfoxide are added and the reaction mixture is stirred at room temperature for 24 hours. The solvent is then evaporated under reduced pressure at a temperature below 35° C and the residue is dissolved in 10 ml. of water. The neutral products are extracted with ethyl acetate:ether (1:1) (6 × 10 ml.). The aqueous phase is acidified with saturated aqueous oxalic acid solution to pH 2, and extracted several times with a mixture of pentane:ether (1:1). The combined organic acid extracts are washed with saturated sodium chloride solution, dried over magnesium sulfate and evaporated to dryness at a temperature not higher than 20° C. Purification of the residue by thin-layer chromatography using chloroform:methanol 9:1 as eluant, affords the pure 10,11-cyclohexanonide of 9α,10α,11α-trihydroxy-15α-tetrahydropyranyloxyprosta-5,13-dienoic acid (10,11-cyclohexanonide-15-tetrahydropyranylether of 10α-hydroxy-PGF$_{2\alpha}$).

Hydrolysis of the tetrahydropyranyloxy group with 65% wt. aqueous acetic acid, in accordance with the method of Example 13 yields the 10,11-cyclohexanonide of 10α-hydroxy PGF$_{2\alpha}$.

EXAMPLE 24

Two hundred milligrams of the 10,11-cyclohexanonide of 9α,10α,11α-trihydroxy-15α-tetrahydropyranyloxyprosta-5,13-dienoic acid are oxidized with an 8N solution of chromic acid in acetone, in accordance with the method of Example 15, to produce the 10,11-cyclohexanonide of 9-keto-10α,11α-dihydroxy-15α-tetrahydropyranyloxyprosta-5,13-dienoic acid, which is then purified by thin-layer chromatography.

The tetrahydropyranyloxy moiety is then cleaved with acetic acid-water (65:35), in accordance with the method of Example 13 affording the 10,11-cyclohexanonide of 10α-hydroxy PGE$_2$.

EXAMPLE 25

Example 19 is repeated but using the 10,11-cyclohexanonide of 9α,10α,11α-trihydroxy-15α-tetrahydropyranyloxyprosta-5,13-dienoic acid as starting material, to produce the 10,11-cylohexanonide-15-tetrahydropyranylether of 10α-hydroxy PGF$_{1\alpha}$, which is then treated with 65% acetic acid, in accordance with the method of Example 13 to yield the 10,11-cyclohexanonide of 10α-hydroxy PGF$_{1\alpha}$.

In a similar manner, the 10,11-cyclohexanonide-15-tetrahydropyranylether of 10α-hydroxy PGE$_2$ is converted to the 10,11-cyclohexanonide of 10α-hydroxy PGE$_1$.

EXAMPLE 26

To a solution of 5 g. of (2'α-hydroxy-3'α,4'α-isopropylidenedioxy-5'β-benzyloxymethylcyclopent-1'α-yl)-acetic acid 1,2'-lactone in 150 ml. of anhydrous toluene, cooled to −60° C is added dropwise, in a 15 minute period, a solution of 3 g. of diisobutylaluminum hydride in 15 ml. of anhydrous toluene at −60° C. After the addition of reagent the reaction mixture is stirred for an additional 15 minutes at −60° C. The mixture is then diluted with methanol until the evolution of gas ceases, and then stirred for 15 minutes at room temperature and diluted with ether. The organic phase is separated, washed with saturated aqueous sodium chloride solution, dried over magnesium sulfate and evaporated to dryness at about 0° C affording (2'α-hydroxy-3'α,-4'α-isopropylidenedioxy-5'β-benzyloxymethylcyclopent-1'α-yl)-acetaldehyde 1,2'-hemiacetal.

In a similar manner (2'α-hydroxy-3'α,4'α-isopropylidenedioxy-5'β-methoxymethylcyclopent-1'α-yl)-acetic acid 1,2'-lactone is converted into (2'α-hydroxy-3'α,4'α-isopropylidenedioxy-5'β-methoxymethylcyclopent-1'α-yl)-acetaldehyde 1,2'-acetal.

EXAMPLE 27

By following the method of Example 12, (2'α-hydroxy-3'α,4'α-isopropylidenedioxy-5'β-benzyloxymethylcyclopent-1'α-yl)-acetaldehyde 1,2'-hemiacetal and (2'α-hydroxy-3'α,4'α-isopropylidenedioxy-5'β-methoxymethylcyclopent-1'α-yl)-acetaldehyde 1,2'-hemiacetal are respectively condensed with the Wittig reagent derived from 5-triphenylphosphoniopentanoic acid and sodium methylsulfinylcarbanion in dimethylsulfoxide solution, to produce respectively 7-(2'α-hydroxy-3'α,4'α-isopropylidenedioxy-5'β-benzyloxymethylcyclopent-1'α-yl)-hept-5-enoic acid and 7-(2'α-hydroxy-3'α,4'α-isopropylidenedioxy-5'β-methoxymethylcyclopent-1'α-yl)-hept-5-enoic acid.

The acid products are then respectively divided into three equal portions, two portions of each acid are successively etherified with dihydropyran and esterified with diazomethane, in accordance with the methods of Examples 10 and 17, respectively, to produce 7-(2'α-tetrahydropyranyloxy-3'α,4'α-isopropylidenedioxy-5'β-benzyloxymethylcyclopent-1'α-yl)-hept-5-enoic acid methyl ester and 7-(2'α-tetrahydropyranyloxy-3'α,4'α-isopropylidenedioxy-5'β-methoxymethylcyclopent-1'α-yl)-hept-5-enoic acid methyl ester, respectively.

The third portion of each acid are respectively esterified with diazomethane in accordance with the method of Example 17. One gram of each of the esterified product is respectively added to a mixture containing 4 ml. of pyridine and 2 ml. of acetic anhydride at room temperature. The respective mixtures are allowed to stand at room temperature for 15 hours and then concentrated by evaporation under vacuum. The respective residues are purified by thin-layer chromatography affording respectively:

7-(2'α-acetoxy-3'α,4'α-isopropylidenedioxy-5'β-benzyloxymethylcyclopent-1'α-yl)-hept-5-enoic acid methyl ester; and 7-(2'α-acetoxy-3'α,4'α-isopropylidenedioxy-5'β-methoxy-methylcyclopent-1'α-yl)-hept-3-enoic acid methyl ester.

EXAMPLE 28

A mixture containing 1.7 g. of zinc dust and 0.26 g. of cuprous chloride in 40 ml. of ethyl ether is stirred and heated at reflux, under a nitrogen atmosphere for 30 minutes. A mixture containing 0.01 moles of 7-(2'α-tetrahydropyranyloxy-3'α,4'α-isopropylidenedioxy-5'β-benzyloxymethylcyclopent-1'α-yl)-hept-5-enoic acid methyl ester is added and then 1.05 ml. of methylene diiodide is added to the refluxing mixture. The resulting mixture is monitored and maintained at reflux until thin-layer chromatographic analysis indicates the reaction to be complete. The reaction mixture is then cooled, washed with water then with dilute aqueous sodium bicarbonate solution and then dried over sodium sulfate and concentrated by evaporation. The residue is purified by chromatography over silica gel eluting with ethyl ether:methylene chloride (1:9) to yield 5α,6α-methylene-7-(2'α-tetrahydropyranyloxy-3'α,4'α-isopropylidenedioxy-5'β-benzyloxymethylcyclopent-1'α-yl)-heptanoic acid methyl ester and 5β,6β-methylene-7-(2'α-tetrahydropyranyloxy-3'α,4'α-isopropylidenedioxy-5'β-benzyloxymethylcyclopent-1'α-yl)-heptanoic acid methyl ester.

Similarily, 5α,6α-methylene-7-(2'α-tetrahydropyranyloxy-3'α,4'α-isopropylidenedioxy-5'β-methoxymethylcyclopent-1'α-yl)-heptanoic acid methyl ester and its 5β,6β-methyl isomer are prepared by following the same procedure but using 7-(2'α-tetrahydropyranyloxy-3'α,4'α-isopropylidenedioxy-5'β-methoxy-methylcyclopent-1'α-yl)-hept-5-enoic acid as the starting material.

EXAMPLE 29

From a solution of 3.4 g. of sodium difluorochloroacetate in 30 ml. of diglyme (distilled over potassium hydroxide pellets), about 10 ml. of the diglyme is distilled off at 30° to 40° C in vacuum. The remaining solution is transferred to a dropping funnel which is placed onto a 3-neck flask. In the flask, 1 g. of 7-(2'α-tetrahydropyranyloxy-3'α,4'α-isopropylidenedioxy-5'β-benzyloxymethylcyclopent-1'α-yl)-hept-5-enoic acid methyl ester is dissolved in 17 ml. of diglyme and heated to the boiling point. The sodium salt solution is added dropwise within 30 minutes while a total of 20 ml. of diglyme is distilled from the reaction mixture at normal pressure. The reaction mixture is refluxed for ten minutes, cooled, filtered and evaporated.

The residue is dissolved in 10 ml. of methanol and then treated with a solution of 2 g. of potassium carbonate in 6 ml. of water. The resulting mixture is refluxed for one hour, then cooled to room temperature and filtered. The filtrate is concentrated by vacuum evaporation, and the concentrate purified by preparative thin-layer chromatography affording 5α,6α-difluoromethylene-7-(2'α-hydroxy-3'α,4'α-isopropylidenedioxy-5'β-benzyloxymethylcyclopent-1'α-yl)-heptanoic acid and 5β,6β-difluoromethylene-7-(2'α-hydroxy-3'α,4'α-isopropylidenedioxy-5'β-benzyloxymethylcyclopent-1'α-yl)-heptanoic acid. This product is in turn treated sequentially with diazomethane and dihydropyran according to the procedures of Examples 10 and 17, respectively, to yield 5α,6α-difluoromethylene-9-(2'α-tetrahydropyranyloxy-3'α,4'α-isopropylidenedioxy-5'β-benzyloxymethylcyclopent-1'α-yl)-heptanoic acid methyl ester and 5β,6β-difluoromethylene-7-(2'α-tetrahydropyranyloxy-3'α,4'α-isopropylidenedioxy-5'β-benzyloxymethylcyclopent-1'α-yl)-heptanoic acid methyl ester which are then further purified by preparative thin-layer chromatography in hexane-ethyl acetate.

Similarly, starting from 9-(2'α-tetrahydropyranyloxy-3'α,4'α-isopropylidenedioxy-5'β-methoxymethylcyclopent-1'α-yl)-hept-5-enoic acid methyl ester there are produced 5α,6α-difluoromethylene-7-(2'α-tetrahydropyranyloxy-3'α,4'α-isopropylidenedioxy-5'β-methoxymethylcyclopent-1'α-yl)-heptanoic acid methyl ester and its 5β,6β-difluoromethylene isomer and also the corresponding parent 2'α-hydroxy heptanoic acids.

EXAMPLE 29a

From a solution of 3.4 g. of sodium difluorochloroacetate in 30 ml. of diglyme (distilled over potassium hydroxide pellets), about 10 ml. of the diglyme is distilled off at 30° to 40° C in vacuum. The remaining solution is transferred to a dropping funnel which is placed onto a 3-neck flask. In the flask, 1 g. of 7-[2'α-acetoxy-3'α,4'α-isopropylidenedioxy-5'β-benzyloxymethylcyclopent-1'α-yl]-hept-5-enoic acid methyl ester is dissolved in 17 ml. of diglyme and heated to the boiling point. The sodium salt solution is added dropwise within 30 minutes while a total of 20 ml. of diglyme is distilled from the reaction mixture at normal pressure. The reaction mixture is refluxed for ten minutes, cooled, filtered and evaporated. The residue is dissolved in 10 ml. of methanol and then treated with a solution containing 1 g. of potassium bicarbonate in 10 ml. of water. The mixture is allowed to stand at room temperature for 15 hours and then evaporated under vacuum and extracted with ethyl acetate. The ethyl acetate extracts are evaporated affording a residue containing 5α,6α-difluoromethylene-7-(2'α-hydroxy-3'α,4'α-isopropylidenedioxy-5'β-benzyloxymethylcyclopent-1'α-yl)-heptanoic acid methyl ester and 5β,6β-difluoromethylene-7-(2'α-hydroxy-3'α,4'α-isopropylidenedioxy-5'β-benzyloxymethylcyclopent-1'α-yl)-heptanoic acid methyl ester, which is then further purified by preparative thin-layer chromatography eluting with hexane-ethyl acetate. This product is then treated with dihydropyran according to the procedure of Example 10 to yield 5α,6α-difluoromethylene-7-(2'α-tetrahydropyranyloxy-3'α,4'α-isopropylidenedioxy-5'β-benzyloxymethylcyclopent-1'α-yl)-heptanoic acid methyl ester and 5β,6β-difluoromethylene-7-(2'α-tetrahydropyranyloxy-3'α-4'α-isopropylidenedioxy-5'β-benzyloxymethylcyclopent-1'α-yl)-heptanoic acid methyl ester, which is further purified by thin-layer chromatography.

Similarly, starting from 7-(2'α-acetoxy-3'α,4'α-isopropylidenedioxy-5'β-methoxymethylcyclopent-1'α-yl)-hept-5-enoic acid methyl ester there are produced 5α,6α-difluoromethylene-7-(2'α-tetrahydropyranyloxy-3'α,4'α-isopropylidenedioxy-5'β-methoxymethylcyclopent-1'α-yl)-heptanoic acid methyl ester and its 5β,6β-difluoromethylene isomer and also the parent 2'α-hydroxy heptanoic acid methyl esters.

EXAMPLE 30

To a refluxing solution of 1 g. of 7-[2'α-tetrahydropyranyloxy-3'α,4'α-isopropylidenedioxy-5'β-benzyloxymethylcyclopent-1'α-yl]-hept-5-enoic acid methyl ester in 10 ml. of diethylene glycol dimethyl ether is added over a one hour period in dropwise fashion with stirring, a solution of 35 equivalents of sodium fluorodichloroacetate in 40 ml. of diethylene glycol dimethyl ether. After refluxing for an additional hour, the mixture is filtered. The filtrate is evaporated to dryness, and the residue is dissolved in 10 ml. of methanol and then treated with a solution of 2 g. of potassium carbonate in 6 ml. of water. The resulting mixture is refluxed for one hour, then cooled to room temperature and filtered. The filtrate is concentrated by vacuum evaporation and the concentrate purified by preparative thin-layer chromatography affording 5α,6α-chlorofluoromethylene-7-(2'α-hydroxy-3'α,4'α-isopropylidenedioxy-5'β-benzyloxymethylcyclopent-1'α-yl)-heptanoic acid and 5β,6β-chlorofluoromethylene-7-(2'α-hydroxy-3' α,4'α-isopropylidenedioxy-5'β-benzyloxymethylcyclopent-1'αyl)-heptanoic acid. This product is in turn treated sequentially with diazomethane and dihydropyran according to the procedures of Examples 10 and 17, respectively, to yield 5α,6α-chlorofluoromethylene-7-(2'α-tetrahydropyranyloxy-3'α,4'α-isopropylidenedioxy-5'β-benzyloxymethylcyclopent-1'α-yl)-heptanoic acid methyl ester and its 5β,6β-chlorofluoromethylene isomer.

In a similar manner but using sodium trichloroacetate in place of sodium fluorodichloroacetate, there are obtained 5α,6α-dichloromethylene-7-[(2'α-tetrahydropyranyloxy-3'α,4'α-isopropylidenedioxy-5'β-benzyloxy ethyl)-cyclopent-1'α-yl]-heptanoic acid methyl ester and 5β,6β-dichloromethylene-7-[(2'α-tetrahydropyranyloxy-3'α,4'α-isopropylidenedioxy-5'β-benzyloxymethyl)-cyclopent-1'α-yl]-heptanoic acid methyl ester and also the parent 2'α-hydroxy heptanoic acids.

Similarly by following the above procedures but using 7-(2'α-tetrahydropyranyloxy-3'α,4'α-isopropylidenedioxy-5'β-methoxymethylcyclopent-1'α-yl)-hept-5-enoic acid methyl ester as the starting material, the following compounds, and also the corresponding 2'α-hydroxy-heptanoic acids, are respectively prepared:

5α,6α-chlorofluoromethylene-7-(2'α-tetrahydropyranyloxy-3'α,4'α-isopropylidenedioxy-5'β-methoxymethylcyclopent-1'α-yl)-heptanoic acid methyl ester;

5β,6β-chlorofluoromethylene-7-(2'α-tetrahydropyranyloxy-3'α,4'α-isopropylidenedioxy-5'β-methoxymethylcyclopent-1'α-yl)-heptanoic acid methyl ester;

5α,6α-dichloromethylene-7-(2'α-tetrahydropyranyloxy-3'α,4'α-isopropylidenedioxy-5'β-methoxymethylcyclopent-1'α-yl)-heptanoic acid methyl ester; and 5β,6β-dichloromethylene-7-(2'α-tetrahydropyranyloxy-3'α,4'α-isopropylidenedioxy-5'β-methoxymethylcyclopent-1'α-yl)-heptanoic acid methyl ester.

EXAMPLE 30a

To a refluxing solution of 1 g. of 7-(2'α-acetoxy-3'α,-4'α-isopropylidenedioxy-5'β-benzyloxymethylcyclopent-1'α-yl)hept-5-enoic acid methyl ester in 10 ml. of diethylene glycol dimethyl ether is added over a one hour period in dropwise fashion with stirring, a solution of 35 equivalents of sodium fluorodichloroacetate in 40 ml. of diethylene glycol dimethyl ether. After refluxing for an additional hour, the mixture is filtered. The filtrate is evaporated to dryness. The residue is dissolved in 10 ml. of methanol and then treated with a solution containing 1 g. of potassium bicarbonate in 10 ml. of water. The mixture is allowed to stand at room temperature for 15 hours and then evaporated under vacuum and extracted with ethyl acetate. The ethyl acetate extracts are evaporated affording a residue containing 5α,6α-chlorofluoromethylene-7-(2'α-hydroxy-3'α,4'α-isopropylidenedioxy-5'β-benzyloxymethylcyclopent-1'α-yl)-heptanoic acid methyl ester and 5β,6β-chlorofluoromethylene-7-(2'α -hydroxy-3'α,4'α-isopropylidenedioxy-5'β-benzyloxymethylcyclopent-1'α-yl)-heptanoic acid methyl ester, which is then further purified by thin-layer chromatography. This product is then treated with dihydropyran according to the procedure of Example 10 to yield 5α,6α-chlorofluoromethylene-7-(2'α-tetrahydropyranyloxy-3'α,4'α-isopropylidenedioxy-5'β-benzyloxymethylcyclopent-1'α-yl)-heptanoic acid methyl ester and 5β,6β-chlorofluoromethylene-7-(2'α-tetrahydropyranyloxy-3'α,4'α-isopropylidenedioxy-5'β-benzyloxymethylcyclopent-1'α-yl)-heptanoic acid methyl ester.

In a similar manner but using sodium trichloroacetate in place of sodium fluorodichloroacetate there are obtained 5α,6α-dichloromethylene-7-(2'α-tetrahydropyranyloxy-3'α,4'α-isopropylidenedioxy-5'β-benzyloxymethylcyclopent-1'α-yl)heptanoic acid methyl ester and 5β,6β-dichloromethylene-7-(2'α-tetrahydropyranyloxy-3'α,4'α-isopropylidenedioxy-5'β-benzyloxymethylcyclopent-1'α-yl)-heptanoic acid methyl ester and the corresponding parent 2'α-hydroxy methyl esters.

Similarly by following the above procedures but using 7-(2'α-acetoxy-3'α,4'α-isopropylidenedioxy-5'β-methoxymethylcyclopent-1'α-yl)-hept-5-enoic acid methyl esters as starting material, the following compounds, and their corresponding parent 2'α-hydroxy methyl esters, are respectively prepared:

5α,6α-chlorofluoromethylene-7-(2'α-tetrahydropyranyloxy-3'α,4'α-isopropylidenedioxy-5'β-methoxymethylcyclopent-1'α-yl)-heptanoic acid methyl ester;

5β,6β-chlorofluoromethylene-7-(2'α-tetrahydropyranyloxy-3'α,4'α-isopropylidenedioxy-5'β-methoxymethylcyclopent-1'α-yl)-heptanoic acid methyl ester;

5α,6α-dichloromethylene-7-(2'α-tetrahydropyranyloxy-3'α,4'α-isopropylidenedioxy-5'β-methoxymethylcyclopent-1'α-yl)-heptanoic acid methyl ester; and 5β,6β-dichloromethylene-7-(2'α-tetrahydropyranyloxy-3'α,4'α-isopropylidenedioxy-5'β-methoxymethylcyclopent-1'α-yl)-heptanoic acid methyl ester.

EXAMPLE 31

To a stirred mixture of 1.4 equivalents of phenyl (trifluoromethyl) mercury and 3.5 equivalents of dried sodium iodide in 30 ml. of benzene is added 0.5 g. of 7-(2'α-tetrahydropyranyloxy-3'α,4'α-isopropylidenedioxy-5'β-benzyloxymethylcyclopent-1'α-yl)-hept-5-enoic acid methyl ester, and the mixture is refluxed under nitrogen atmosphere. The mixture is monitored and refluxing continued until t.l.c. analysis indicates the reaction to be complete. The reaction mixture is then cooled to room temperature and filtered. The filtrate is evaporated to dryness under reduced pressure and the residue is purified by thin-layer chromatography, thus obtaining 5α,6α-difluoromethylene-7-(2'α-tetrahydropyranyloxy-3'α,4'α-isopropylidenedioxy-5'β-benzyloxymethylcyclopent-1'α-yl)heptanoic acid methyl ester and 5β,6β-difluoromethylene-7-(2'α-tetrahydropyranyloxy-3'α,4'α-isopropylidenedioxy-5'β-benzyloxymethylcyclopent-1'α-yl)-heptanoic acid methyl ester.

Similarly by following the same procedure but using 7-(2'α-tetrahydropyranyloxy-3'α,4'α-isopropylidenedioxy-5'β-methoxymethylcyclopent-1'α-yl)-hept-5-enoic acid methyl ester as starting material, there is prepared 5α,6α-difluoromethylene-7-(2'α-tetrahydropyranyloxy-3'α,4'α-isopropylidenedioxy-5'β-methoxymethylcyclopent-1'α-yl)-heptanoic acid methyl ester and 5β,6β-difluoromethylene-7-(2'α-tetrahydropyranyloxy-3'α,4'α-isopropylidenedioxy-5'β-methoxymethylcyclopent-1'α-yl)-heptanoic acid methyl ester.

EXAMPLE 31a

To a stirred mixture of 1.4 equivalents of phenyl (trifluoromethyl) mercury and 3.5 equivalents of dried sodium iodide in 30 ml. of benzene is added 0.5 g. of 7-(2'α-acetoxy-3'α,4'α-isopropylidenedioxy-5'β-benzyloxymethylcyclopent-1'α-yl)-hept-5-enoic acid methyl ester, and the mixture is refluxed in nitrogen atmosphere until t.l.c. analysis indicates the reaction to be complete. Thereafter, the reaction mixture is cooled to room temperature and filtered. The filtrate is evaporated to dryness under reduced pressure and the residue is purified by thin-layer chromatography yielding 5α,6α-difluoromethylene-7-(2'α-acetoxy-3'α,4'α-isopropylidenedioxy-5'β-benzyloxymethylcyclopent-1'α-yl)-heptanoic acid methyl ester and 5β,6β-difluoromethylene-7-(2'α-acetoxy-3'α,4'α-isopropylidenedioxy-5'β-benzyloxymethylcyclopent-1'α-yl)-heptanoic acid methyl ester.

Similarly, starting from 7-(2'α-acetoxy-3'α,4'α-isopropylidenedioxy-5'β-methoxymethylcyclopent-1'α-yl)-hept-5-enoic acid methyl ester there are produced 5α,6α-difluoromethylene-7-(2'α-tetrahydropyranyloxy-3'α,4'α-isopropylidenedioxy-5'β-methoxymethylcyclopent-1'α-yl)-heptanoic acid methyl ester and its 5β,6β-difluoromethylene isomer and also the parent 2'α-hydroxy heptanoic acid methyl esters.

EXAMPLE 32

To a prehydrogenated suspension of 250 mg. of 10% palladium charcoal catalyst in 20 ml. of acetone (distilled first from potassium permanganate and then from chromium trioxide) is added 1 g. of 5α,6α-methylene-7-(2'α-tetrahydropyranyloxy-3'α,4'α-isopropylidenedioxy-5'β-benzyloxymethylcyclopent-1'α-yl)-heptanoic acid methyl ester in 20 ml. of acetone and the mixture is stirred under hydrogen atmosphere until the absorption of hydrogen ceases. The catalyst is then separated by filtration and washed with acetone. The combined organic solutions are evaporated to dryness under reduced pressure. The residue is purified by chromatography on Florisil, to obtain the pure 5α,6α-methylene-7-(2'α-tetrahydropyranyloxy-3'α,4'α-isopropylidenedioxy-5'β-hydroxymethylcyclopent-1'α-yl)-heptanoic acid methyl ester.

By the same method the following compounds are obtained from the corresponding 5'β-benzyloxymethyl derivatives:

5β,6β-methylene-7-(2'α-tetrahydropyranyloxy-3'α,4'α-isopropylidenedioxy-5'β-hydroxymethylcyclopent-1'α-yl)-heptanoic acid methyl ester;

5α,6α-difluoromethylene-7-(2'α-tetrahydropyranyloxy-3'α,4'α-isopropylidenedioxy-5'β-hydroxymethylcyclopent-1'α-yl)-heptanoic acid methyl ester;

5α,6α-dichloromethylene-7-(2'α-tetrahydropyranyloxy-3'α,4'α-isopropylidenedioxy-5'β-hydroxymethylcyclopent-1'α-yl)-heptanoic acid methyl ester;

5α,6α-chlorofluoromethylene-7-(2'α-tetrahydropyranyloxy-3'α,4'α-isopropylidenedioxy-5'β-hydroxymethylcyclopent-1'α-yl)-heptanoic acid methyl ester; as well as the corresponding 5β,6β-dihalomethylene isomers.

EXAMPLE 33

A stirred solution of 1.5 g. of 5α,6α-methylene-7-(2'α-tetrahydropyranyloxy-3'α,4'α-isopropylidenedioxy-5'β-methoxymethylcyclopent-1'α-yl)-heptanoic acid methyl ester in 20 ml. of anhydrous methylene chloride is cooled to −78° C in a dry ice-acetone bath and treated with 25 ml. of boron tribromide. The stirred mixture is allowed to warm rapidly to 0° C and kept at this temperature for 50 minutes. The excess boron tribromide is decomposed by the addition of ether, while maintaining the reaction mixture at 0° C. It is then poured into a vigorously stirred slurry of 9.5 g. of sodium bicarbonate in 50 ml. of a saturated aqueous solution of sodium potassium tartrate; the organic layer is separated and the aqueous phase extracted with methylene chloride. The combined organic extracts are dried over magnesium sulfate and evaporated to dryness under reduced pressure. The residue is purified by crystallization from chloroform to afford 5α,6α-methylene-7-(2'α-tetrahydropyranyloxy-3'α,4'α-isopropylidenedioxy-5'β-hydroxymethylcyclopent-1'α-yl)-heptanoic acid methyl ester.

EXAMPLE 34

To a suspension of 1.1 g. of diatomaceous earth (dried for 24 hours at 105° C) and 500 mg. of the chromium trioxidedipyridine complex in 5.2 ml. of anhydrous methylene chloride, cooled to −5° C, are added under stirring 600 mg. of 5α,6α-methylene-7-(2'α-tetrahydropyranyloxy-3'α,4'α-isopropylidenedioxy-5'β-hydroxymethylcyclopent-1'α-yl)-heptanoic acid methyl ester and the mixture is stirred for 10 minutes further, maintaining the temperature between −5° C and 0° C; 1.6 g. of sodium bisulfite monohydrate is then added and the mixture is stirred for an additional 10 minute period, filtered through magnesium sulfate and the solids washed with methylene chloride, receiving the filtrate in a flask cooled to −60° C in a dry ice-acetone bath. The combined filtrates are evaporated to dryness under reduced pressure, at a temperature below 0° C, obtaining 5α,6α-methylene-7-(2'α-tetrahydropyranyloxy- 3'α,4'α-isopropylidenedioxy-5'β-formylcyclopent-1'α-yl)-heptanoic acid methyl ester, which is then further purified by thin-layer chromatography.

In a similar manner, but using as starting materials the corresponding 5'β-hydroxymethyl compounds obtained in Example 32, there are produced:

5β,6β-methylene-7-(2'α-tetrahydropyranyloxy-3'α,-4'α-isopropylidenedioxy-5'β-formylcyclopent-1'α-yl)-heptanoic acid methyl ester;

5α,6α-difluoromethylene-7-(2'α-tetrahydropyranyloxy-3'α,4'α-isopropylidenedioxy-5'β-formylcyclopent-1'α-yl)-heptanoic acid methyl ester;

5α,6α-dichloromethylene-7-(2'α-tetrahydropyranyloxy-3'α,4'α-isopropylidenedioxy-5'β-formylcyclopent-1'α-yl)heptanoic acid methyl ester;

5β,6β-dichloromethylene-7-(2'α-tetrahydropyranyloxy-3'α,4'α-isopropylidenedioxy-5'β-formylcyclopent-1'α-yl)heptanoic acid methyl ester;

5α,6α-chlorofluoromethylene-7-(2'α-tetrahydropyranyloxy-3'α,4'α-isopropylidenedioxy-5'β-formylcyclopent-1'α-yl)heptanoic acid methyl ester; and 5β,6β-chlorofluoromethylene-7-(2'α-tetrahydropyranyloxy-3'α,4'α-isopropylidenedioxy-5'β-formylcyclopent-1'α-yl)heptanoic acid methyl ester.

EXAMPLE 35

To a suspension of 135 mg. of sodium hydride (previously washed with pentane, under argon) in 40 ml. of dimethoxyethane freshly distilled from lithium aluminum hydride is added, under stirring and under an atmosphere of argon, a solution of 666 mg. of dimethyl-2-oxoheptylphosphonate in 15 ml. of dimethoxyethane. The reaction mixture is stirred for 30 minutes at room temperature and 500 mg. of 5α,6α-methylene-7-(2'α-tetrahydropyranyloxy-3'α,4'α-isopropylidenedioxy-5'β-formylcyclopent-1'α-yl)-heptanoic acid methyl ester are added. The reaction mixture is stirred at room temperature for 2 hours further, it is then carefully neutralized with acetic acid (to pH 7) and evaporated to dryness under reduced pressure at a temperature below 30° C. The residue is purified by chromatographic techniques, thus obtaining the pure 5α,6α-methylene-9α-tetrahydropyranyloxy-10α,11α-isopropylidenedioxy-15-ketoprost-13-enoic acid methyl ester.

Likewise the following compounds are produced:

5β,6β-methylene-9α-tetrahydropyranyloxy-10α,11α-isopropylidenedioxy-15-ketoprost-13-enoic acid methyl ester;

5α,6α-difluoromethylene-9α-tetrahydropyranyloxy-10α,11α-propylidenedioxy-15-ketoprost-13-enoic acid methyl ester;

5β,6β-difluoromethylene-9α-tetrahydripyranyloxy-10α,11α-isopropylidenedioxy-15-ketoprost-13-enoic acid methyl ester;

5α,6α-dichloromethylene-9α-tetrahydripyranyloxy-10α,11α-isopropylidenedioxy-15-ketoprost-13-enoic acid methyl ester;

5β,6β-dichloromethylene-9α-tetrahydropyranyloxy-10α,11α-isopropylidenedioxy-15-ketoprost-13-enoic acid methyl ester;

5α,6α-chlorofluoromethylene-9α-tetrahydropyranyloxy-10α,11α-isopropylidenedioxy-15-ketoprost-13-enoic acid methyl ester; and 5β,6β-chlorofluoromethylene-9α-tetrahydropyranyloxy-10α,11α-isopropylidenedioxy-15-ketoprost-13-enoic acid methyl ester.

EXAMPLE 36

To a stirred solution of 400 mg. of 5α,6α-methylene-9α-tetrahydropyranyloxy-10α,11α-isopropylidenedioxy-15-ketoprost-13-enoic acid methyl ester in 5 ml. of dimethoxyethane freshly distilled from lithium aluminum hydride are added 1.5 ml. of zinc borohydride reagent in anhydrous dimethoxyethane. The reaction mixture is stirred for an hour at room temperature, and treated with a saturated solution of sodium bitartrate until the evolution of gas ceases. It is then diluted with methylene chloride, dried over magnesium sulfate and evaporated to dryness under vacuo at a temperature below 30° C, to yield 5α,6α-methylene-9α-tetrahydropyranyloxy-10α,11α-isopropylidenedioxy-15α-hydroxyprost-13-enoic acid methyl ester in mixture with the 15β-hydroxy isomer.

The individual isomers are separated by thin-layer chromatography.

By the same meehod the remaining 15-keto products obtained in Example 35 are converted into the corresponding 15α- and 15β-hydroxy derivatives.

EXAMPLE 37

To a solution of 100 mg. of 5α,6α-methylene-9α-tetrahydropyranyloxy-10α,11α-isopropylidenedioxy-15α-hydroxyprost-13-enoic acid methyl ester in 0.3 ml. of tetrahydrofuran is added 2.5 ml. of acetic acid-water (65:35), and the reaction mixture is stirred during 6 hours at room temperature. The solvents are then eliminated by distillation under reduced pressure, and the oily residue purified by thin-layer chromatography, to afford 5α,6α-methylene-9α,15α-dihydroxy-10α,11α-isopropylidenedioxyprost-13-enoic acid methyl ester.

To a solution of 50 mg. of 5α,6α-methylene-9α,15α-dihydroxy-10α,11α-isopropylidenedioxyprost-13-enoic acid methyl ester in 10 ml. of methanol are added 17 mg. of anhydrous potassium carbonate and the reaction mixture is stirred at room temperature for 5 hours. It is then cooled to 0° C and neutralized with acetic acid, diluted with cold sodium chloride solution and extracted several times with methylene chloride. The combined organic extracts are dried over magnesium sulfate and evaporated to dryness under reduced pressure, to obtain 5α,6α-methylene-9α,15α-dihydroxy-10α,11α-isopropylidenedioxyprost-13-enoic acid.

In a similar manner the following compounds are produced:

5β,6β-methylene-9α,15α-dihydroxy-10α,11α-isopropylidenedioxyprost-13-enoic acid;

5α,6α-difluoromethylene-9α,15α-dihydroxy-10α,11α-isopropylidenedioxyprost-13-enoic acid;

5β,6β-difluoromethylene-9α,15α-dihydroxy-10α,11α-isopropylidenedioxyprost-13-enoic acid;

5α,6α-dichloromethylene-9α,15α-dihydroxy-10α,11α-isopropylidenedioxyprost-13-enoic acid;

5β,6β-dichloromethylene-9α,15α-dihydroxy-10α,11α-isopropylidenedioxyprost-13-enoic acid;

5α,6α-chlorofluoromethylene-9α,15α-dihydroxy-10α,11α-isopropylidenedioxyprost-13-enoic acid; and 5β,6β-chlorofluoromethylene-9α,15α-dihydroxy-10α,11α-isopropylidenedioyxprost-13-enoic acid.

EXAMPLE 38

By following the saponification method of Example 37, 200 mg. of 5α,6α-methylene-9α-tetrahydropyranyloxy-10α,11α-isopropylidenedioxy-15α-hydroxyprost-13-enoic acid methyl ester is converted into the free acid.

A mixture of 100 mg. of 5α,6α-methylene-9α-tetrahydropyranyloxy-10α,11α-isopropylidenedioxy-15α-hydroxyprost-13-enoic acid, 0.5 ml. of pyridine and 0.5 ml. of acetic anhydride is kept at room temperature for 1 hour and evaporated to dryness under reduced pressure to produce 5α,6α-methylene-9α-tetrahydropyranyloxy-10α,11α-isopropylidenedioxy-15α-acetoxyprost-13-enoic acid, which upon treatment with acetic acid water (65:35), in accordance with the method of Example 13 affords 5α,6α-methylene-9α-hydroxy-10α,11α-isopropylidenedioxy-15α-acetoxyprost-13-enoic acid.

The latter compound is then oxidized with Jones' reagent, in accordance with the method of Example 15, thus producing 5α,6α-methylene-9-keto-10α,11α-isopropylidenedioxy-15α-acetoxyprost-13-enoic acid.

In a similar manner but using 5α,6α-difluoromethylene-9α-tetrahydropyranyloxy-10α,11α-isopropylidenedioxy-15α-hydroxyprost-13-enoic acid methyl ester as starting material, there is obtained 5α,6α-difluoromethylene-9-keto-10α,11α-isopropylidenedioxy-15α-acetoxyprost-13-enoic acid.

EXAMPLE 39

Example 16 is repeated but using 5α,6α-methylene-9α-tetrahydropyranyloxy-10α,11α-isopropylidenedioxy-15α-hydroxyprost-13-enoic acid methyl ester and 5α,6α-difluoromethylene-9α-tetrahydropyranyloxy-10α,11α-isopropylidenedioxy-15α-hydroxyprost-13-enoic acid methyl ester as starting materials, to yield respectively 5α,6α-methylene-9α,10α,11α,15α-tetrahydroxyprost-13-enoic acid methyl ester and 5α,6α-difluoromethylene-9α,10α,11α,15α-tetrahydroxyprost-13-enoic acid methyl ester, which are converted into the corresponding free acids by saponification with 1.1 molar equivalents of potassium carbonate, in accordance with the method of Example 37.

EXAMPLE 40

A mixture of 100 mg. of 9α,15α-dihydroxy-10α,11α-isopropylidenedioxyprosta-5,13-dienoic acid, 0.4 ml. of pyridine and 0.8 ml. of acetic anhydride is kept at room temperature for 1 hour. The reaction mixture is then evaporated to dryness under reduced pressure and the residue is dissolved in ethyl acetate. 50 Mg. of sodium bisulfate are added and the solution is filtered through diatomaceous earth. The filtrate is evaporated to dryness to yield 9α,15α-diacetoxy-10α,11α-isopropylidenedioxyprosta-5,13-dienoic acid.

By the same process but using propionic, caproic and cyclopentylpropionic anhydride as esterifying agents, there are respectively obtained the 9α,15α-dipropionoxy-, 9α,15α-dicaproxy- and 9α,15α-dicyclopentylpropionxy- derivatives of 10α,11α-isopropylidenedioxyprosta-5,13-dienoic acid.

In a similar manner are esterified the other prostanoic acid derivatives having one or more free hydroxy groups obtained in the preceding Examples (12–14, 19, 23, 25 and 37–39). Representative compounds thus obtained are:

9-keto-10α,11α-isopropylidenedioxy-15α-acetoxyprosta-5,13-dienoic acid;

9α,15α-diacetoxy-10α,11α-isopropylidenedioxyprost-13-enoic acid;

9-keto-10α,11α-15α-triacetoxyprosta-5,13-dienoic acid;

5α,6α-methylene-9α,15α-dipropionoxy-10α,11α-isopropylidenedioxyprost-13-enoic acid;

9α,10α,11α,15α-tetrapropionoxyprosta-5,13-dienoic acid; and

5α,6α-difluoromethylene-9α,10α,11α,15α-tetracaproxyprost-13-enoic acid; etc.

EXAMPLE 41

A solution of 5 g. of 7-(2'α-tetrahydropyranyloxy-3'α,4'α-isopropylidenedioxy-5'β-benzyloxymethylcyclopent-1'α-yl)-hept-5-enoic acid methyl ester in 100 ml. of ethyl acetate is hydrogenated in the presence of 1 g. of 10% palladium charcoal catalyst until the uptake of hydrogen ceases. The catalyst is then separated by filtration, washed with ethyl acetate and the combined filtrates evaporated to dryness, thus obtaining 7-(2'α-tetrahydropyranyloxy-3'α,4'α-isopropylidenedioxy-5''β-hydroxymethylcyclopent-1'α-yl)-heptanoic acid methyl ester.

The foregoing compound is then submitted to the procedures described in Examples 6, 7, 8 and 13, to produce successively:

9-(2'α-tetrahydropyranyloxy-3'α,4'α-isopropylidenedioxy-5'β-formylcyclopent-1'α-yl)-heptanoic acid methyl ester;

9α-tetrahydropyranyloxy-10α,11α-isopropylidenedioxy-15-ketoprost-13-enoic acid methyl ester;

9α-tetrahydropyranyloxy-10α,11α-isopropylidenedioxy-15α-hydroxyprost-13-enoic acid methyl ester; and 9α,15α-dihydroxy-10α,11α-isopropylidenedioxyprost-13-enoic acid methyl ester.

EXAMPLE 42

To a solution of 100 mg. of 9α,15α-dihydroxy-10α,11α-isopropylidenedioxyprosta-5,13-dienoic acid in 10 ml. of methanol is added 2.6 ml. of a 0.1N solution of sodium hydroxide, and the mixture is stirred at room temperature for 1 hour. It is then evaported to dryness under reduced pressure, to give the sodium salt of 9α,15α-dihydroxy-10α,11α-isopropylidenedioxyprosta-5,13-dienoic acid.

By employing 1.1 molar equivalents of potassium hydroxide (in the form of a 0.1N solution) in place of sodium hydroxide in the above procedure, the potassium salt of 9α,15α-dihydroxy-10α,11α-isopropylidenedioxyprosta-5,13-dienoic acid is obtained.

Similarly, the sodium and potassium salts of the prostanoic acid derivative products of Examples 12–16, 19, 23–25 and 37–39 are produced.

EXAMPLE 43

To a solution of 100 mg. of 9α,15α-dihydroxy-10α,11α-isopropylidenedioxyprosta-5,13-dienoic acid in 10 ml. of methanol is added a mixture of 3 ml. of concentrated ammonium hydroxide solution and 5 ml. of methanol. The resulting mixture is stirred for two hours at room temperature and then evaporated to dryness, to yield 9α,15α-dihydroxy-10α,11α-isopropylidenedioxyprosta-5,13-dienoic acid ammonium salt.

By employing dimethylamine, diethylamine, dipropylamine, and piperidine in place of ammonium hydroxide in the above process, the corresponding N,N-dimethylamine; N,N-diethylamine; N,N-dipropylamine and piperidine salts of 9α,15α-dihydroxy-10α,11α-isopropylidenedioxyprosta-5,13-dienoic acid are obtained.

In a similar manner, respectively using ammonia, dimethylamine, diethylamine, dipropylamine and piperidine and the prostanoic acid derivative products, respectively, of Examples 12–16, 19, 23–25 and 37–39, the corresponding ammonium amide; N,N-dimethylamine; N,N-diethylamine; N,N-dipropylamine; and piperidine salts of these acids are prepared.

Obviously many modifications and variations of the invention, described herein above and below, can be made without departing from the essence and scope thereof.

What is claimed is:

1. A compound of the formula:

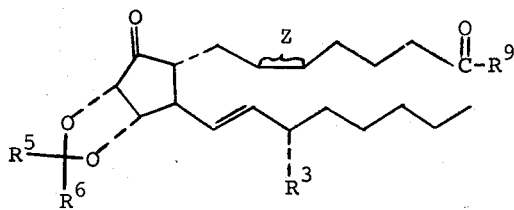

wherein $R^3$ is selected from the group consisting of hydroxy or a hydrocarbon carboxylic acyloxy group having from two through 12 carbon atoms or a grouping selected from those consisting of methoxy, ethoxy, propoxy, 2-propoxy, cyclopropoxy, butoxy, 2-butoxy, t-butoxy, cyclobutoxy, pentoxy, 3-pentoxy, cyclopentoxy, hexoxy, cyclohexoxy, methoxy-methoxy, 2-methoxy-ethoxy, 2-ethoxy-ethoxy, 2-aminoethoxy, 2-chloroethoxy, 3-fluorobutoxy, 2-acetoxyethoxy, 3-nitropropoxy, 3-aminocyclobutoxy, 4-hexylcyclohexoxy, 2-phenoxyethoxy, phenoxy, tolyloxy, chlorophenoxy, m,m'-dimethylphenoxy, p-nitrophenoxy, β-chloropropoxy, p-aminophenoxy, tetrahydrofuran-2'-yloxy and tetrahydropyran-2'-yloxy; Z represents a saturated carbon-carbon linkage or a cis carbon=carbon double bond; $R^5$ and $R^6$ are independently selected from the group of hydrogen, lower alkyl and aryl groups having a total of up to 16 carbon atoms and containing one aromatic ring having up to 10 carbon atoms optionally substituted with one or more pharmaceutically acceptable functional groups selected from the group of hydroxy, lower alkyl hydrolyzable ester, lower alkyl or halo, or $R^5$ and $R^6$ together with the carbon atom to which they are joined from a cycloalkyl group having 5 or 6 ring carbon atoms; $R^9$ is hydroxy; or the group

is a carboalkoxy group having from two to 12 carbon atoms; and pharmaceutically acceptable addition salts thereof.

2. The compound of claim 1 and pharmaceutically acceptable addition salts thereof wherein $R^3$ is selected from the group consisting of hydroxy and a hydrocarbon carboxylic acyloxy group having from 2 through 12 carbon atoms.

3. The compound of claim 2 and pharmaceutically acceptable addition salts thereof wherein $R^3$ is selected from the group consisting of hydroxy and acetoxy.

4. The compound of claim 1 and pharmaceutically acceptable addition salts thereof wherein $R^5$ and $R^6$ are each methyl.

5. The compound of claim 1 and pharmaceutically acceptable addition salts thereof wherein $R^9$ is hydroxy.

6. The compound of claim 1 wherein the group

is a carboalkoxy group having from 2 through 7 carbon atoms.

7. The compound of claim 1 and pharmaceutically acceptable addition salts thereof wherein Z is a saturated carbon-carbon linkage.

8. The compound of claim 7 and pharmaceutically acceptable addition salts thereof wherein $R^9$ is hydroxy.

9. The compound of claim 1 and pharmaceutically acceptable addition salts thereof wherein Z is a cis carbon=carbon double bond.

10. The compound of claim 9 and pharmaceutically acceptable addition salts thereof wherein $R^9$ is hydroxy.

11. The compound of claim 1 and pharmaceutically acceptable addition salts thereof wherein said compound is 9-keto-10α,11α-isopropylidenedioxy-15α-hydroxyprosta-5,13-dienoic acid.

12. The compound of claim 1 and pharmaceutically acceptable addition salts thereof wherein said compound is 9-keto-10α,11α-isopropylidenedioxy-15α-hydroxyprost-13-enoic acid.

13. The pharmaceutically acceptable addition salts of claim 1.

14. The salts of claim 1 wherein said salts is a sodium salt.

* * * * *